United States Patent
Ozawa et al.

(10) Patent No.: US 11,607,142 B2
(45) Date of Patent: Mar. 21, 2023

(54) BIOSENSOR ARRANGEMENT STRUCTURE

(71) Applicant: TS TECH CO., LTD., Asaka (JP)

(72) Inventors: Hidetoshi Ozawa, Shioya-gun (JP);
Takayoshi Ito, Shioya-gun (JP);
Kazuyuki Takasawa, Shioya-gun (JP);
Akira Miyoshi, Shioya-gun (JP);
Munetaka Kowa, Shioya-gun (JP)

(73) Assignee: TS TECH CO., LTD., Asaka (JP)

( * ) Notice: Subject to any disclaimer, the term of this patent is extended or adjusted under 35 U.S.C. 154(b) by 429 days.

(21) Appl. No.: 16/633,124

(22) PCT Filed: Jul. 27, 2018

(86) PCT No.: PCT/JP2018/028177
§ 371 (c)(1),
(2) Date: Jan. 22, 2020

(87) PCT Pub. No.: WO2019/035337
PCT Pub. Date: Feb. 21, 2019

(65) Prior Publication Data
US 2021/0153754 A1 May 27, 2021

(30) Foreign Application Priority Data

Aug. 15, 2017 (JP) .............................. JP2017-156695
Aug. 17, 2017 (JP) .............................. JP2017-157300
(Continued)

(51) Int. Cl.
*A61B 5/021* (2006.01)
*B60N 2/75* (2018.01)
(Continued)

(52) U.S. Cl.
CPC ........ *A61B 5/02108* (2013.01); *A61B 5/0059* (2013.01); *A61B 5/6893* (2013.01);
(Continued)

(58) Field of Classification Search
CPC . A61B 5/02108; A61B 5/0059; A61B 5/6893; A61B 2503/22; B60N 2/75;
(Continued)

(56) References Cited

U.S. PATENT DOCUMENTS 6,240,309 B1 5/2001 Yamashita et al.
2006/0020216 A1* 1/2006 Oishi .................. A61B 5/0285
600/500

(Continued)

FOREIGN PATENT DOCUMENTS

JP  H09-149894 A  6/1997
JP  H10-155749 A  6/1998
(Continued)

OTHER PUBLICATIONS

English Translation for JP2013000177A (Year: 2022).*
(Continued)

*Primary Examiner* — Mahmoud S Ismail
(74) *Attorney, Agent, or Firm* — Oliff PLC

(57) ABSTRACT

Disclosed is a biosensor arrangement structure, including: a plurality of biosensors that is disposed in a seat for supporting an occupant and that measures a health condition of the occupant. The seat includes: a seat body for holding the occupant; and an auxiliary supporter for supporting a body part of the occupant except for a torso and thighs. At least one of the plurality of biosensors is disposed at the auxiliary supporter.

20 Claims, 28 Drawing Sheets

(30) Foreign Application Priority Data

Aug. 17, 2017 (JP) .............................. JP2017-157347
Aug. 17, 2017 (JP) .............................. JP2017-157348

(51) Int. Cl.

| | | |
|---|---|---|
| B60N 2/80 | (2018.01) | |
| B60W 60/00 | (2020.01) | |
| A61B 5/00 | (2006.01) | |
| B60N 2/00 | (2006.01) | |
| B60W 40/08 | (2012.01) | |

(52) U.S. Cl.

CPC .............. *B60N 2/002* (2013.01); *B60N 2/75* (2018.02); *B60N 2/80* (2018.02); *B60W 40/08* (2013.01); *B60W 60/0053* (2020.02); *A61B 2503/22* (2013.01); *B60W 2540/221* (2020.02)

(58) Field of Classification Search

CPC ..... B60N 2/80; B60N 2/002; B60W 60/0053; B60W 40/08; B60W 2540/221
USPC ........................................................ 600/480
See application file for complete search history.

(56) References Cited

U.S. PATENT DOCUMENTS

| | | | |
|---|---|---|---|
| 2008/0228046 A1 | 9/2008 | Futatsuyama et al. | |
| 2019/0031061 A1* | 1/2019 | Reith | B60N 2/5635 |
| 2019/0351800 A1* | 11/2019 | Seibold | B60N 2/0224 |

FOREIGN PATENT DOCUMENTS

| | | | |
|---|---|---|---|
| JP | 2000-107141 A | | 4/2000 |
| JP | 2002-017510 A | | 1/2002 |
| JP | 2002-315728 A | | 10/2002 |
| JP | 2002-329300 A | | 11/2002 |
| JP | 2003-235829 A | | 8/2003 |
| JP | 2003235829 A | * | 8/2003 |
| JP | 2005-168908 A | | 6/2005 |
| JP | 2005-312653 A | | 11/2005 |
| JP | 2006-026211 A | | 2/2006 |
| JP | 2007-531579 A | | 11/2007 |
| JP | 2008-234009 A | | 10/2008 |
| JP | 2009-261419 A | | 11/2009 |
| JP | 2011-123653 A | | 6/2011 |
| JP | 2011-183050 A | | 9/2011 |
| JP | 2012-196335 A | | 10/2012 |
| JP | 2013-000177 A | | 1/2013 |
| JP | 2013000177 A | * | 1/2013 |
| JP | 5181741 B2 | | 4/2013 |
| JP | 2013-147225 A | | 8/2013 |
| JP | 2014-008846 A | | 1/2014 |
| JP | 5691237 B2 | | 4/2015 |
| JP | 2016-077890 A | | 5/2016 |
| JP | 2016-091309 A | | 5/2016 |
| JP | 2016-159081 A | | 9/2016 |
| JP | 2016-168177 A | | 9/2016 |
| JP | 2016-186821 A | | 10/2016 |
| JP | 2016-190022 A | | 11/2016 |
| JP | 2017-060584 A | | 3/2017 |
| JP | 2017-109616 A | | 6/2017 |
| JP | 2017109616 A | * | 6/2017 |
| JP | 2017-131445 A | | 8/2017 |

OTHER PUBLICATIONS

English Translation for JP2003235829A (Year: 2022).*
English Translation for JP2017109616A (Year: 2022).*
Jul. 6, 2021 Office Action issued in Japanese Patent Application No. 2017-157300.
Oct. 9, 2018 International Search Report issued in International Patent Application No. PCT/JP2018/028177.
Mar. 8, 2022 Office Action issued in Japanese Patent Application No. 2017-157300.
Aug. 10, 2021 Office Action issued in Japanese Patent Application No. 2017-156695.
Aug. 31, 2021 Office Action issued in Japanese Patent Application No. 2017-157348.
Jun. 1, 2021 Office Action issued in Japanese Patent Application No. 2017-157347.
Feb. 18, 2020 International Preliminary Report on Patentability issued in International Patent Application No. PCT/JP2018/028177.
May 10, 2022 Office Action issued in Japanese Patent Application No. 2017-157348.
Dec. 20, 2022 Office Action issued in Japanese Patent Application No. 2017-157348.

* cited by examiner

BIOSENSOR ARRANGEMENT STRUCTURE

CROSS-REFERENCE TO RELATED APPLICATIONS

The entire discloses of Japanese Patent Applications No. 2017-156695 filed on Aug. 15, 2017, No. 2017-157300 filed on Aug. 17, 2017, No. 2017-157347 filed on Aug. 17, 2017, and No. 2017-157348 filed on Aug. 17, 2017 are incorporated herein by reference in their entirety.

TECHNICAL FIELD

The present invention relates to a biosensor arrangement structure.

BACKGROUND ART

When the health condition of a driver deteriorates while he/she is driving a vehicle, the deterioration may sometimes have a negative impact on driving of the vehicle. To cope with the problem, it is desired to detect deterioration of the health condition and to take some measures in advance. One of such measures is a technique known in the art that involves estimating the biological information such as blood flow and blood pressure from measurement results such as pulse waves by non-contact blood flow sensors embedded in the sitting surface and the backseat surface of a seat, so as to understand the health condition of a driver (see Patent Document 1).

CITATION LIST

Patent Literature

Patent Document 1: JP 2016-168177A

SUMMARY OF INVENTION

Technical Problem

In the technique disclosed in Patent Document 1, the blood flow in the popliteal artery and the thoracic aorta of a subject in a seat is measured to obtain blood flow data, and the blood pressure in the popliteal artery and the thoracic aorta of the subject is individually calculated from the blood flow data.

However, when the subject in the seat is a driver of a vehicle, the back of the knee where the popliteal artery runs sometimes be separated from the seat. When the subject in the seat is not a driver of a vehicle or when the seat is not a vehicle seat, the blood pressure cannot always be measured with high accuracy since the sitting posture is unlikely to be stable.

The present invention has been made in view of the above-described circumstances, and an object thereof is to provide a biosensor arrangement structure that can improve the accuracy in measuring the health condition of a subject in a seat.

Solution to Problem

In order to solve the above-described problem, the invention recited in claim 1 is a biosensor arrangement structure, including: a plurality of biosensors that is disposed in a seat for supporting an occupant and that measures a health condition of the occupant, wherein the seat includes: a seat body for holding the occupant; and an auxiliary supporter for supporting a body part of the occupant except for a torso and thighs, and wherein at least one of the plurality of biosensors is disposed at the auxiliary supporter.

The invention recited in claim 2 is the biosensor arrangement structure according to claim 1, wherein the auxiliary supporter includes an arm rest for supporting an arm of the occupant, and wherein a front upper end of the arm rest is a part where the at least one of the plurality of biosensors is installed.

The invention recited in claim 3 is the biosensor arrangement structure according to claim 1, wherein the auxiliary supporter includes a head rest for supporting a head of the occupant, and wherein a front part of the head rest is a part where the at least one of the plurality of biosensors is installed.

The invention recited in claim 4 is the biosensor arrangement structure according to claim 1, wherein the auxiliary supporter includes a neck rest for supporting a neck of the occupant, and wherein a front part of the neck rest is a part where the at least one of the plurality of biosensors is installed.

The invention recited in claim 5 is the biosensor arrangement structure according to claim 1, wherein the auxiliary supporter includes an ottoman for supporting legs of the occupant, and wherein a right and/or left part of the ottoman is a part where the at least one of the plurality of biosensors is installed.

The invention recited in claim 6 is the biosensor arrangement structure according to claim 1, wherein the auxiliary supporter includes a foot rest for supporting feet of the occupant, and wherein a right and/or left part of the foot rest is a part where the at least one of the plurality of biosensors is installed.

The invention recited in claim 7 is the biosensor arrangement structure according to claim 1, wherein the plurality of biosensors includes a pulse wave sensor for estimating a blood pressure of the occupant.

The invention recited in claim 8 is the biosensor arrangement structure according to claim 7, wherein the pulse wave sensor is a photoelectric pulse wave sensor that uses light to measure a pulse wave of the occupant.

The invention recited in claim 9 is the biosensor arrangement structure according to claim 8, wherein the photoelectric pulse wave sensor is exposed on a covering material forming a surface of the seat body or the auxiliary supporter.

The invention recited in claim 10 is the biosensor arrangement structure according to claim 7, wherein the pulse wave sensor is a piezoelectric pulse wave sensor that measures a pressure wave on a body surface of the occupant to measure the pulse wave of the occupant.

The invention recited in claim 11 is the biosensor arrangement structure according to claim 7, wherein the pulse wave sensor is an electromagnetic pulse wave sensor that uses an electromagnetic wave to measure a pulse wave of the occupant.

The invention recited in claim 12 is the biosensor arrangement structure according to claim 7, wherein at least one of the plurality of biosensors is a biosensor of a different type from the pulse wave sensor.

The invention recited in claim 13 is the biosensor arrangement structure according to claim 1, wherein the seat is installed in a vehicle with a driving controller for switching between autonomous driving and manual driving, and the seat is transformable into different forms between in the autonomous driving and in the manual driving.

Advantageous Effects of Invention

According to the invention recited in claim 1, at least one of the plurality of biosensors is disposed at the auxiliary supporter. Therefore, it is possible to obtain the biological information at a plurality of points respectively in the body part supported by the auxiliary supporter with the biosensor and in another body part. This can improve the accuracy in measuring the health condition of the occupant.

According to the invention recited in claim 2, it becomes possible to dispose a biosensor at the arm rest and therefor to obtain the biological information at an arm. Further, since the biosensor can be disposed at such a position that the biosensor is likely to contact the arm, it becomes easier to obtain the biological information at the arm.

According to the invention recited in claim 3, it becomes possible to dispose a biosensor at the head rest and therefor to obtain the biological information at the head. Further, since the biosensor can be disposed at such a position that the biosensor is likely to contact the head, it becomes easier to obtain the biological information at the head According to the invention recited in claim 4, it becomes possible to dispose a biosensor at the neck rest and therefor to obtain the biological information at the neck. Further, since the biosensor can be disposed at such a position that the biosensor is likely to contact the neck, it becomes easier to obtain the biological information at the neck According to the invention recited in claim 5, it becomes possible to dispose a biosensor at the ottoman and therefor to obtain the biological information at the legs. Further, since the biosensor can be disposed at such a position that the biosensor is likely to contact the legs, it becomes easier to obtain the biological information at the legs.

According to the invention recited in claim 6, it becomes possible to dispose a biosensor at the foot rest and therefor to obtain the biological information at the feet. Further, since the biosensor can be disposed at such a position that the biosensor is likely to contact the feet, it becomes easier to obtain the biological information at the feet.

According to the invention recited in claim 7, it is possible to measure the pulse wave of the occupant at a plurality of points by the plurality of biosensors. This can improve the accuracy in estimating the blood pressure of the occupant.

According to the invention recited in claim 8, the pulse wave sensor is a photoelectric pulse wave sensor. This is suitable for measuring the pulse wave at a body part that can be irradiated with light.

According to the invention recited in claim 9, it is possible to prevent light from being blocked by the covering material. This can improve the accuracy in measurement by the photoelectric pulse wave sensor.

According to the invention recited in claim 10, the pulse wave sensor is a piezoelectric pulse wave sensor. This is suitable for measuring the pulse wave at a body part where the pressure wave is measurable.

According to the invention recited in claim 11, the pulse wave sensor is an electromagnetic pulse wave sensor. Therefore, it is possible to measure the pulse wave of the occupant even when the biosensor is not in contact with the occupant body.

According to the invention recited in claim 12, at least one of the plurality of biosensors is a biosensor of a different type from the pulse wave sensor. Therefore, it is possible to obtain a different type of the biological information. This can improve the accuracy in measuring the health condition of the occupant.

According to the invention recited in claim 13, it is possible to make a measurement by the biosensors even when the seat is transformed into different forms between autonomous driving and manual driving. Further, since it is easier to let the body to be supported by the auxiliary supporter during autonomous driving, highly accurate measurement results are likely to be obtained by using the plurality of biosensors.

DESCRIPTION OF EMBODIMENTS

Figure 1:
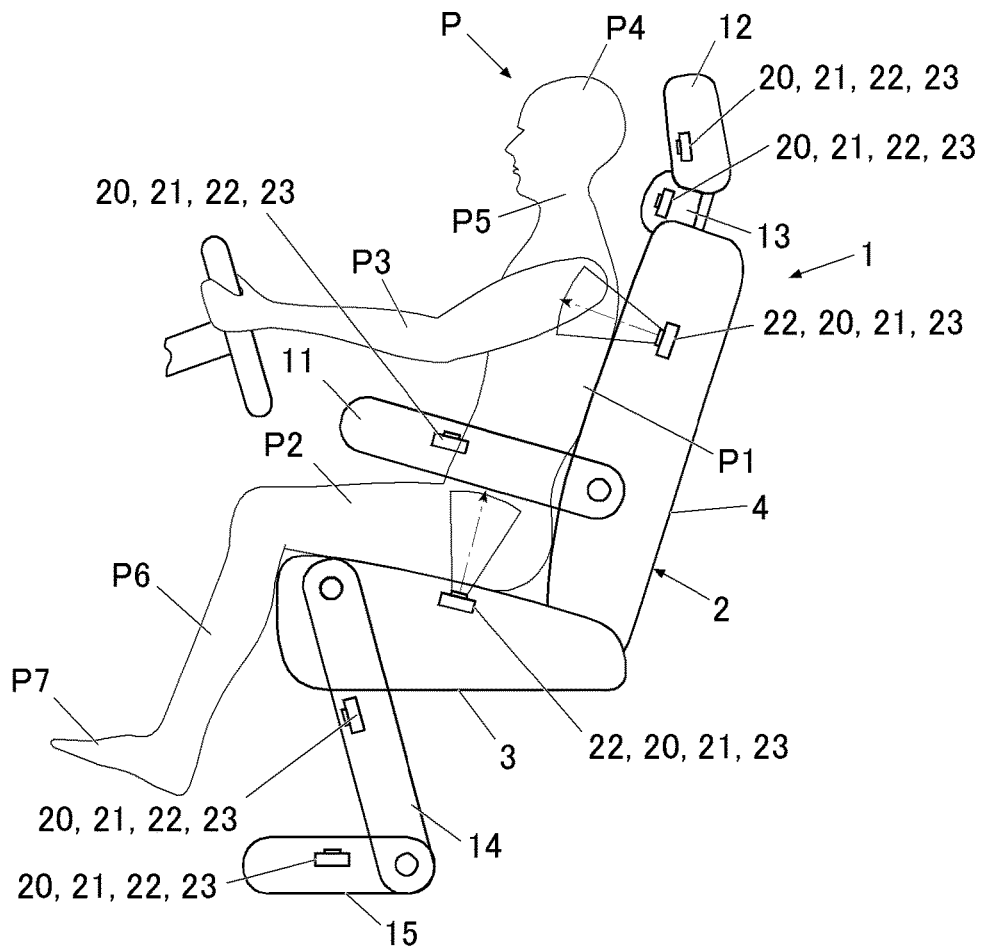
FIG. 1 illustrates an arrangement of a plurality of biosensors provided in a seat.

Hereinafter, embodiments of the present invention will be described referring to the drawings. While the following embodiments includes a variety of limitations that are technically preferable for carrying out the present invention, it is not intended to limit the technical scope of the present invention to the following embodiments and illustrated examples.

Figure 2:
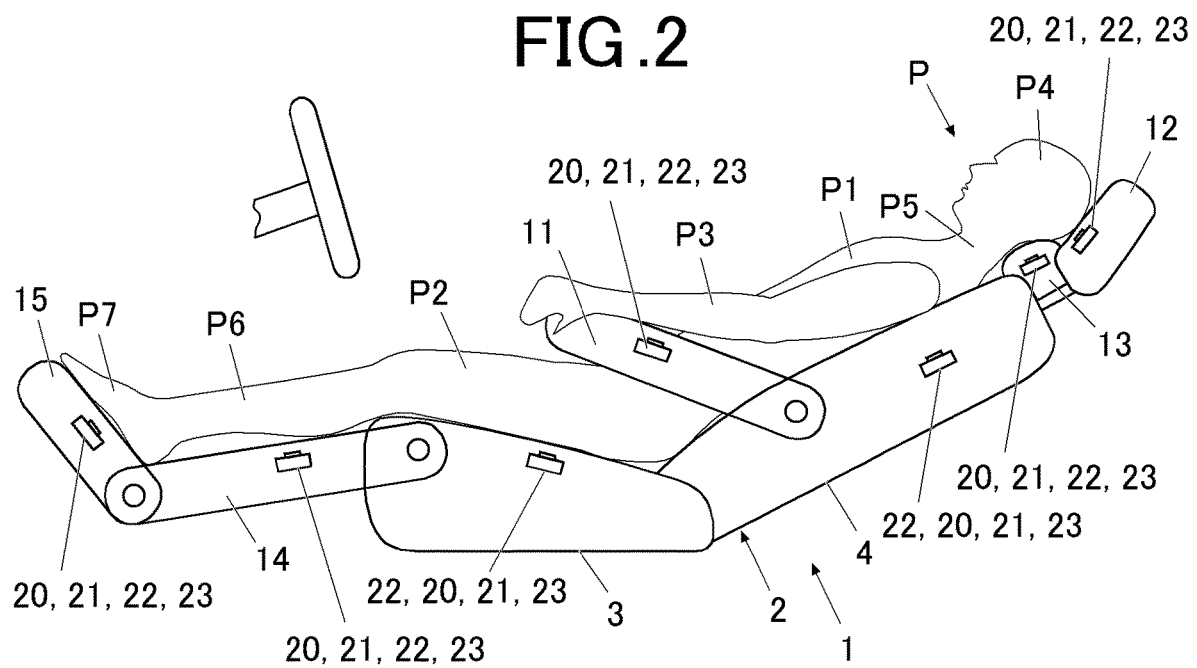
FIG. 2 illustrates the positional relationship between an occupant and the plurality of biosensors when the seat is in a reclined position.

In FIG. 1 and FIG. 2, the reference sign 1 indicates a seat in which a person, who is an occupant P, sits, and which supports the occupant P in the seat. In the embodiment, the seat 1 is provided in a vehicle V such as an automobile. Particularly in the embodiment, the seat 1 is provided in the vehicle V that can switch between autonomous driving and manual driving. The seat 1 is not limited to being installed in such vehicles but may be provided in other types of transportations.

In the embodiment, the vehicle V includes a driving controller V1 that switches between autonomous driving and manual driving, the above-described seat 1 that can be transformed into different forms, and a seat controller (not illustrated in the figures) that controls the movement of the seat 1 when the form is changed. Since the driving controller V1 and the seat controller are linked with each other, the seat 1 is configured to be able to be transformed into different forms between in autonomous driving and in manual driving The driving controller V1 switches from autonomous driving to manual driving, for example, when the vehicle is moved from a highway to a local road or when the vehicle runs into a road having a complicated shape.

The seat 1 includes a seat body 2 for holding the occupant P, and auxiliary supporters 11 to 15 that are accessories of the seat body 2 to support any of body parts P3 to P7 of the occupant P except for the torso P1 and the thighs P2.

The seat body 2 includes a seat cushion 3 for holding the hip and the thighs P2 of the occupant P, and a seat back 4 that is supported at a lower end thereof by the seat cushion 3.

As used herein, the torso P1 of the occupant P includes the shoulder, the chest, the abdomen, the low back and the hip of the occupant P.

The seat cushion 3 includes a seat cushion frame (not shown in the figures) as the frame, a cushion pad 3a provided on the seat cushion frame, and a covering material 3b covering the seat cushion frame and the cushion pad.

The seat back 4 includes a seat back frame (not shown in the figures) as the frame, a cushion pad 4a provided on the seat back frame, and a covering material 4b covering the seat back frame and the cushion pad.

As described above, the plurality of auxiliary supporters 11 to 15 are accessories of the seat body 2, in more detail, the seat cushion 3 and the seat back 4.

That is, the plurality of auxiliary supporters 11 to 15 includes an arm rest 11 for supporting the arm P3 of the occupant P, a head rest 12 for supporting the head P4 of the occupant P, a neck rest 13 for supporting the neck P5 of the occupant P, an ottoman 14 for supporting the legs P6 of the occupant P, and a foot rest 15 for supporting the feet P7 of the occupant P.

In the embodiment, the arm rest 11, the head rest 12, and the neck rest 13 are provided to the seat back 4, and the ottoman 14 and the foot rest 15 are provided to the seat cushion 3.

While the arm rest 11 is provided to the seat back 4 in the embodiment, the configuration is not limited thereto. The arm rest 11 may be provided to the seat cushion 3 via a member such as a bracket.

As with the seat cushion 3 and the seat back 4, each of the plurality of auxiliary supporters 11 to 15 includes a frame, a cushion pad, and a covering material.

Figure 4:
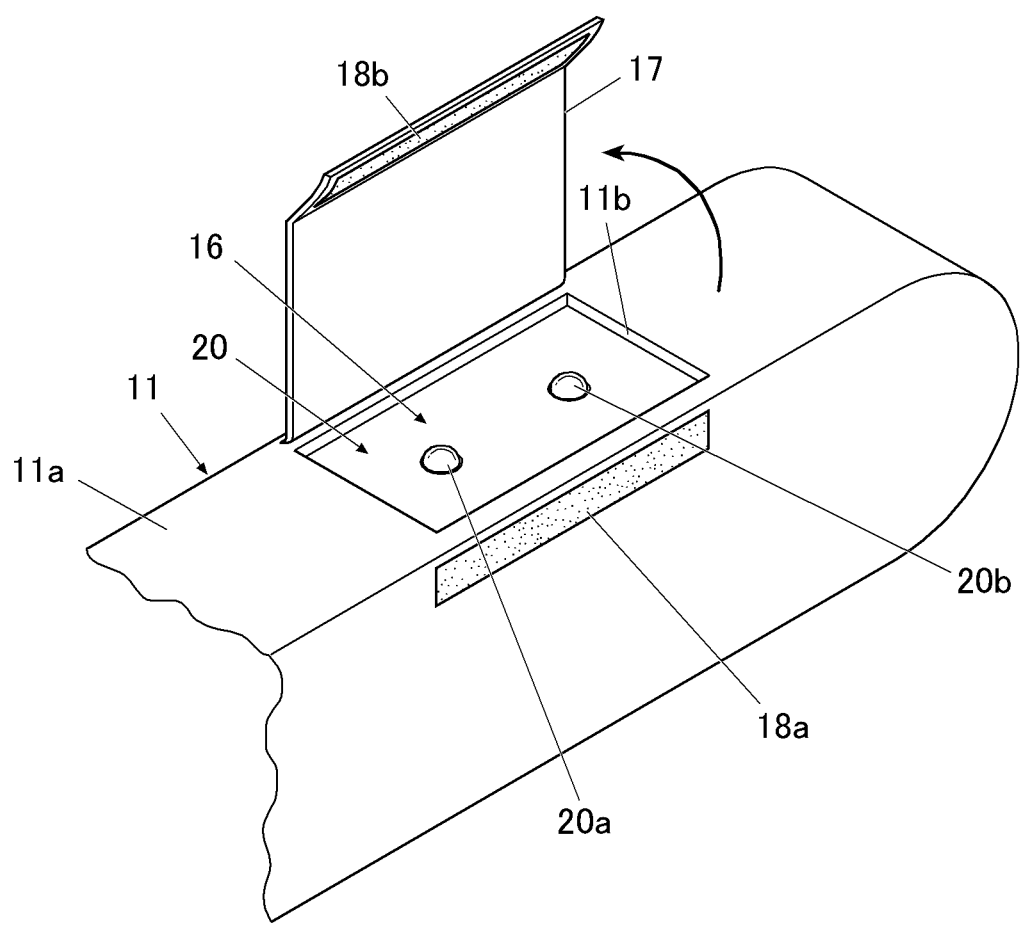
FIG. 4 is a perspective view illustrating installation of a biosensor in an arm rest.

In the example illustrated in FIG. 4, the arm rest 11 explicitly includes a covering material 11a.

In the seat 1 as described above, a plurality of biosensors 20 to 23 are provided to measure the health condition of the occupant P. At least one of the plurality of biosensors 20 to 23 is provided in the auxiliary supporters 11 to 15.

In the embodiment, as illustrated in FIG. 1 and FIG. 2, one or two biosensor(s) 20 to 23 are provided in each of the seat cushion 3, the seat back 4, the arm rest 11, the head rest 12, the neck rest 13, the ottoman 14, and the foot rest 15.

Figure 3:
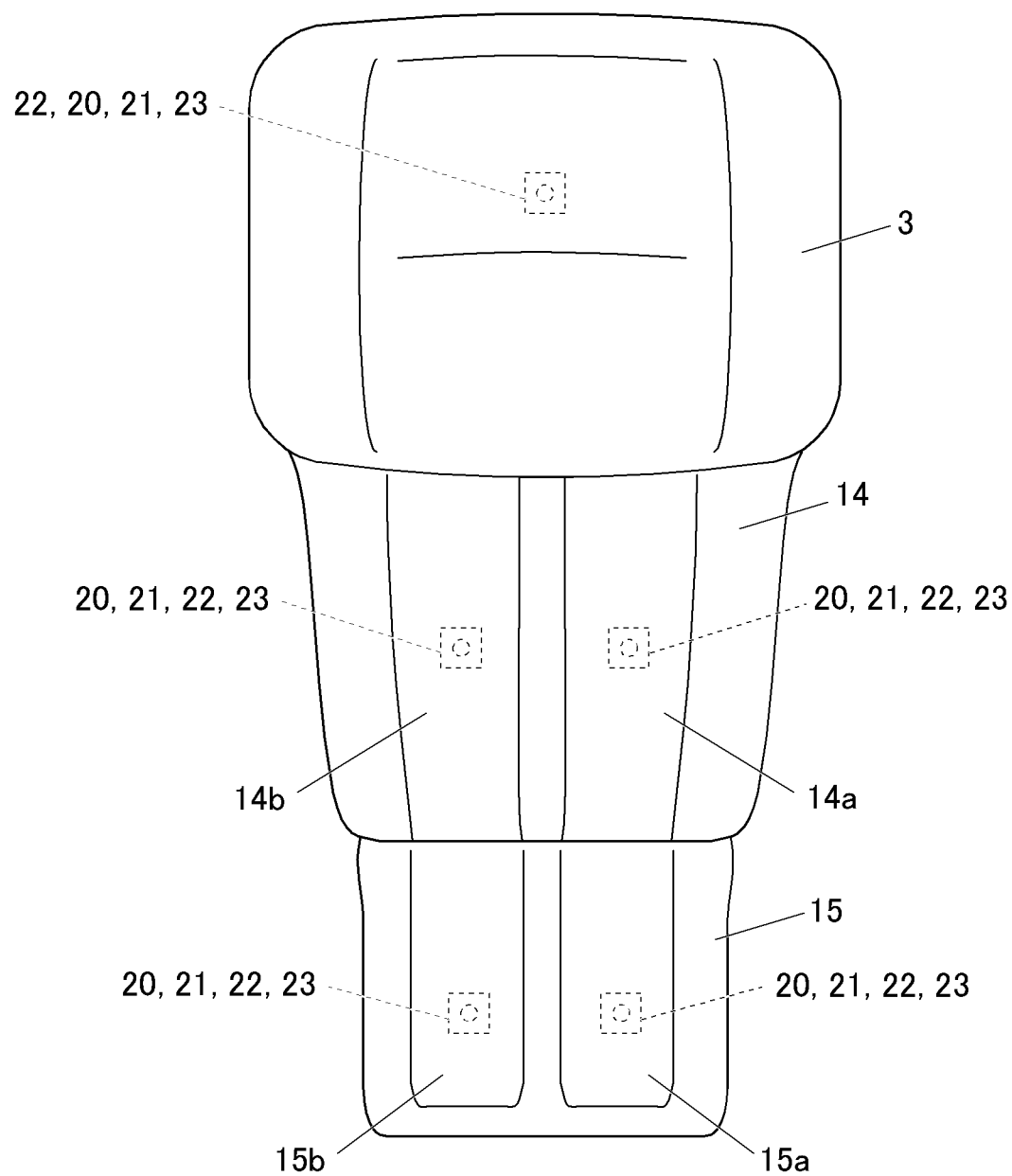
FIG. 3 is a plan view illustrating an arrangement of a plurality of biosensors that is provided in a seat cushion and auxiliary supporters that are accessories of the seat cushion.

As illustrated in FIG. 3, when a biosensor 20 to 23 is provided in the seat cushion 3, the biosensor 20 to 23 is disposed corresponding to the center part between the right and left ischial bones of the hip of the occupant P so that the seat is comfortable. In other words, the biosensor 20 to 23 is disposed at the center part of the portion of the seat cushion 3 on which the hip is positioned. In summary, the biosensor 20 to 23 may be disposed at the position of the hip.

In the embodiment, the single biosensor 20 to 23 is provided at the center of the seat cushion 3. Instead, biosensors 20 to 23 may be provided respectively at right and left portions of the seat cushion 3 corresponding to the right and left thighs P2, P2.

When a biosensor 20 to 23 is provided in the seat back 4, the biosensor 20 to 23 is disposed corresponding to the position of the heart. The thoracic aorta runs in the chest where the heart is located, and this position is preferable for measuring the conditions of blood flow by using the biosensor 20 to 23.

In the embodiment, the biosensor 20 to 23 in the seat back 4 is disposed corresponding to the position of the heart. However, the configuration is not limited thereto, and the biosensor 20 to 23 may be disposed at any position suitable for measuring the conditions of blood flow.

When biosensors 20 to 23 are provided in the plurality of auxiliary supporters 11 to 15, each of the plurality of auxiliary supporters 11 to 15 has a suitable part for obtaining the biological information of the occupant P, and the biosensors 20 to 23 are disposed at the respective suitable parts.

Regarding the arm rest 11, the front upper end of the arm rest 11 is the part where the biosensor 20 to 23 is installed. The front upper end of the arm rest 11 is suitable since it is likely to contact the arm P3 not only while the occupant P is driving but also when he/she is in a reclined position.

Regarding the head rest 12, the front part of the head rest 12 is the part where the biosensor 20 to 23 is installed. The front part of the head rest 12 is suitable since it is likely to contact the head P4 when the occupant P is in a reclined position although it is unlikely to contact the head P4 while the occupant P is driving.

Regarding the neck rest 13, the front part of the neck rest 13 is the part where the biosensor 20 to 23 is installed. The front part of the neck rest 13 is suitable since it is likely to contact the neck P5 when the occupant P is in a reclined position although it is unlikely to contact the neck P5 while the occupant P is driving the vehicle.

Regarding the ottoman 14, the right and left portions 14a, 14b of the ottoman 14 are the parts where the biosensors 20 to 23 are installed as illustrated in FIG. 3, so that the biosensors 20 to 23 correspond to the legs P6, P6. The right and left portions 14a, 14b of the ottoman 14 are suitable since they are likely to contact the legs P6, P6 when the occupant P is in a reclined position although they are unlikely to contact the legs P6, P6 while he/she is driving.

In the embodiment, the thighs P2 and the legs P6 are distinguished from each other, and the legs P6 particularly refer to the lower parts of the legs of the occupant P below the thighs P2 (below the knees).

Regarding the foot rest 15, the right and left portions 15a, 15b of the foot rest 15 are the parts where the biosensors 20 to 23 are installed as illustrated in FIG. 3, so that the biosensors 20 to 23 correspond to the feet P7, P7. The right and left portions 15a, 15b of the foot rest 15 are suitable since they are likely to contact the feet P7, P7 when the occupant P is in a reclined position although they are unlikely to contact the feet P7, P7 while he/she is driving.

The plurality of auxiliary supporters 11 to 15 can be retracted, moved or removed when they are not used. When the seat 1 is in a reclined position as illustrated in FIG. 2, all of the biosensors 20 to 23 provided in the seat 1 are used. However, while the occupant P is driving for example, the condition may not sometimes be preferable for sensing. In particular, the ottoman 14 and the foot rest 15 can prevent the occupant P from driving the vehicle when they are in the position as illustrated in FIG. 2. To cope with the problem, the plurality of auxiliary supporters 11 to 15 are configured to be retractable, movable or removable when they are not used.

When the auxiliary supporters 11 to 15 are removed, it is not preferred that connecting wires such as wire harnesses connecting the biosensors 20 to 23 to a controller and a power supply are cut. To avoid this, the wire harnesses of the embodiment include connectors that allow dividing each wire harness into one and the other portions and reconnecting them with each other. By using such connecting wires such as wire harnesses with connectors, it is possible to temporarily remove the auxiliary supporters 11 to 15 and reattach the auxiliary supporters 11 to 15 to the seat 1.

In the embodiment, the arm rest 11 can be moved away (rotated about a rotation axis) when it is not used. Further, the head rest 12 and the neck rest 13 can be removed, and the ottoman 14 and the foot rest 15 can be retracted. However, the configuration is not limited thereto. The auxiliary supporters 11 to 15 may be individually retractable, movable or removable when they are not used.

The measurement by the biosensors 20 to 23 may be started or stopped at the time the auxiliary supporters 11 to 15 are retracted, moved or removed.

With this configuration, for example, the measurement by the biosensors 20 to 23 can be started when the seat 1 is transformed into the position as illustrated in FIG. 2 in response to the vehicle V being switched to autonomous driving, and the measurement by the biosensors 20 to 23 can be stopped when the seat 1 is returned to the position as illustrated in FIG. 1 in response to the vehicle V being returned to manual driving.

That is, the timing of starting and stopping the measurement by the biosensors 20 to 23 can be linked to the movement of the auxiliary supporters 11 to 15. This eliminates the need of a manual operation by the occupant P for starting or stopping the measurement by the biosensors 20 to 23, which is hassle-free and convenient.

The biosensors 20 to 23, which are provided in the seat body 2 and/or the plurality of auxiliary supporters 11 to 15, include pulse wave sensors 20 to 22 for estimating the blood pressure of the occupant and another type of biosensor 23 that is different from the pulse wave sensors 20 to 22.

Examples of the pulse wave sensors 20 to 22 include a photoelectric pulse wave sensor 20 that measures the pulse wave of the occupant P by using light, a piezoelectric pulse wave sensor 21 that measures the pulse wave of the occupant P by measuring the pressure wave at the body surface of the occupant P, an electromagnetic pulse wave sensor 22 that measures the pulse wave of the occupant P by using electromagnetic waves, and the like.

In the embodiment, any of the various types of pulse wave sensors 20 to 22 may be used. Further, the various types of pulse wave sensors 20 to 22 may be used in any combination.

As illustrated in FIG. 4, the photoelectric pulse wave sensor 20 includes a light emitter 20a and a light receiver 20b. The photoelectric pulse wave sensor 20 measures the pulse wave by emitting light from the light emitter 20a to the body of the occupant P and receiving the reflected light thereof at the light receiver 20b.

Although not shown in the figures, the piezoelectric pulse wave sensor 21 includes a piezoelectric element, a substrate on which the piezoelectric element is mounted, a case enclosing the piezoelectric element, and the like. The piezoelectric pulse wave sensor 21 is close to (in contact with) an object to be measured when making a measurement.

As illustrated in FIG. 1, the electromagnetic pulse wave sensor 22 is a non-contact sensor that emits an electromagnetic wave to the body of the occupant P and detects the biological information based on the reflection wave from the body of the occupant P. The electromagnetic pulse wave sensor 22 can also make a measurement at an unexposed part of the body of the occupant P As used herein, an electromagnetic wave means an electromagnetic wave in a broad sense, including a radio wave of approximately 100 MHz and a microwave as well as infrared light, visible light, ultraviolet light, X ray, and the like. A suitable electromagnetic wave is used within the range in which the human body is not harmed. Such electromagnetic waves have a characteristic of unlikely penetrating through various metals such as iron, copper, and aluminum.

The data on the blood flow condition that is obtained by a measurement using the pulse wave sensors 20 to 22 is suitably subjected to calculation by a blood pressure estimator that is constituted by the above-described operation controller V1 and another controller (which may be an external device such as a computer). The calculation by the blood pressure estimator enables determination of the blood pressure (arterial blood pressure) of the occupant P The blood pressure estimator cooperates with a calculating program stored in a storage (not illustrated in the figures) so as to be able to calculate and determine the blood pressure of the occupant P.

In more detail, the blood pressure can be estimated by a pulse wave propagating time-based blood pressure estimating method known in the art, in which the blood pressure is estimated from the distance between two points where the biosensors 20 to 23 are disposed, which correspond to two parts of the body of the occupant P, and the time lag between the sensed pulse waves at the two points where the biosensors 20 to 23 are disposed. The above-described calculating program is based on the blood pressure estimating method, which is executed by the above-described operation controller V1 or the other controller (see FIG. 6).

In other words, the plurality of biosensors 20 to 23 are disposed at at least two points away from each other of the seat 1 as illustrated in FIG. 1 and FIG. 2, which allows pulse wave data to be detected from at least two points of the body of the occupant P. Compared to a configuration that uses a single biosensor 20 (21 to 23), this configuration can improve the accuracy of estimating the blood pressure from the detected pulse wave data and thereby calculating the health condition of the occupant P.

Figure 6:
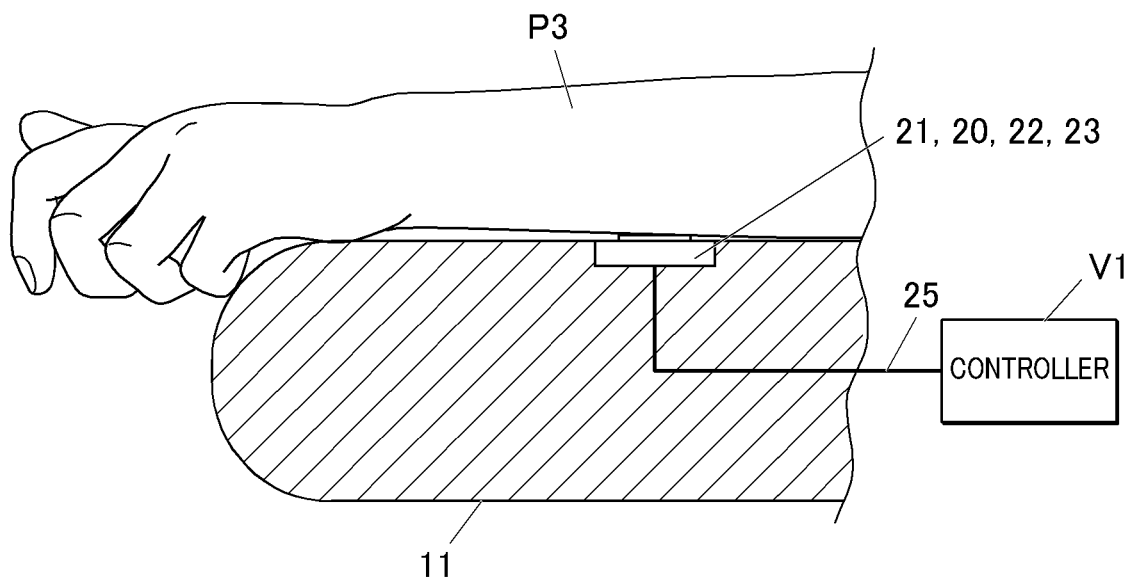
FIG. 6 illustrates the state in which a biosensor is connected to a controller.

As illustrated in FIG. 6, the biosensors 20 to 23 are connected to the above-described operation controller V1 or another controller by communication/connection wires 25 such as wire harnesses. The communication/connection wires 25 are disposed to run inside the seat body 2 and the plurality of auxiliary supporters 11 to 15 (the arm rest 11 in FIG. 6).

Examples of the biosensor 23 of a different type from the biosensors 20 to 22 include various types of sensors such as a blood flow sensor, a heartbeat sensor, a brain-wave sensor, a myoelectric sensor, a non-invasive blood sugar sensor, and a sleepiness sensor, and any of these sensors may be used as the biosensor 23.

However, biosensors that cannot be incorporated in the seat body 2 or the plurality of auxiliary supporters 11 to 15 are excluded.

It is required that the plurality of biosensors 20 to 23 as described above is disposed at a position in the seat 1 where the health condition of the occupant P can be measured as accurately as possible. For this reason, the plurality of biosensors 20 to 23 are each disposed in the seat 1 at a point close to an exposed part of the body of the occupant P or in a position where the measurement is not interfered by a predetermined interference factor.

The photoelectric pulse wave sensor 20, which receives the light emitted to the body of the occupant P and reflected thereon at the light receiver 20b, is suitable for measurement at a part of the body of the occupant P that is likely to be exposed such as the arms P3, the head P4, and the neck P5. For this reason, when the photoelectric pulse wave sensor 20 is provided to the seat 1, the photoelectric pulse wave sensor 20 is exposed on the covering material 3b, 4b, 11a that forms the surface of the seat body 2 or the plurality of auxiliary supporters 11 to 15.

The piezoelectric pulse wave sensor 21, which detects a pressure wave on the body surface of the occupant P by using a piezoelectric element, is suitable for measurement at a part of the body of the occupant P that is likely to be exposed such as the arms P3, the head P4, and the neck P5. For this reason, when the piezoelectric pulse wave sensor 21 is provided to the seat 1, the piezoelectric pulse wave sensor 21 is exposed on the covering material of the seat body 2 or the plurality of auxiliary supporters 11 to 15.

As described above, the electromagnetic pulse wave sensor 22 has a characteristic of unlikely penetrating through various metals such as iron, copper and aluminum. Although not shown in the figures, the seat 1 includes an embedded heater wire for heating the seat 1, which prevents penetration of electromagnetic waves. The electromagnetic pulse wave sensor 22 is disposed in a position aside from such members that prevent penetration of electromagnetic waves.

To be more specific, for example, when at least one biosensor 20 (21 to 23) of the plurality of biosensors 20 to 23 is provided in the arm rest 11, the biosensor 20 (21 to 23) is desirably disposed in a position where it contacts the arm P3 of the occupant P or is close to the arm P3.

Accordingly, in the embodiment, the front upper end of the arm rest 11 is the part where the biosensors 20 to 23 are installed. In the example illustrated in FIG. 4, the arm rest 11 has a housing 16 for housing the photoelectric pulse wave sensor 20 at the front upper end. To be more specific, the covering material 11a has an opening 11b at the front upper end of the arm rest 11, and a space inside the arm rest 11 including the opening 11b serves as the housing 16. The photoelectric pulse wave sensor 20 is housed in the housing 16. The housing 16 (opening 11b) is openable through a single swing cover 17. The distal end of the cover 17 is attachable/detachable by hook and loop fasteners 18a, 18b provided respectively on the distal end of the cover 17 and the covering material 11a of the arm rest 11. The surface of the cover 17 is made of the same material as the covering material 11a.

With the configuration as illustrated in FIG. 4, the photoelectric pulse wave biosensor 20 can be usually hidden, and the photoelectric pulse wave biosensor 20 can be readily exposed at the time of measurement. Instead of the photoelectric pulse wave sensor 20, the piezoelectric pulse wave sensor 21 may be provided.

Figure 5A:
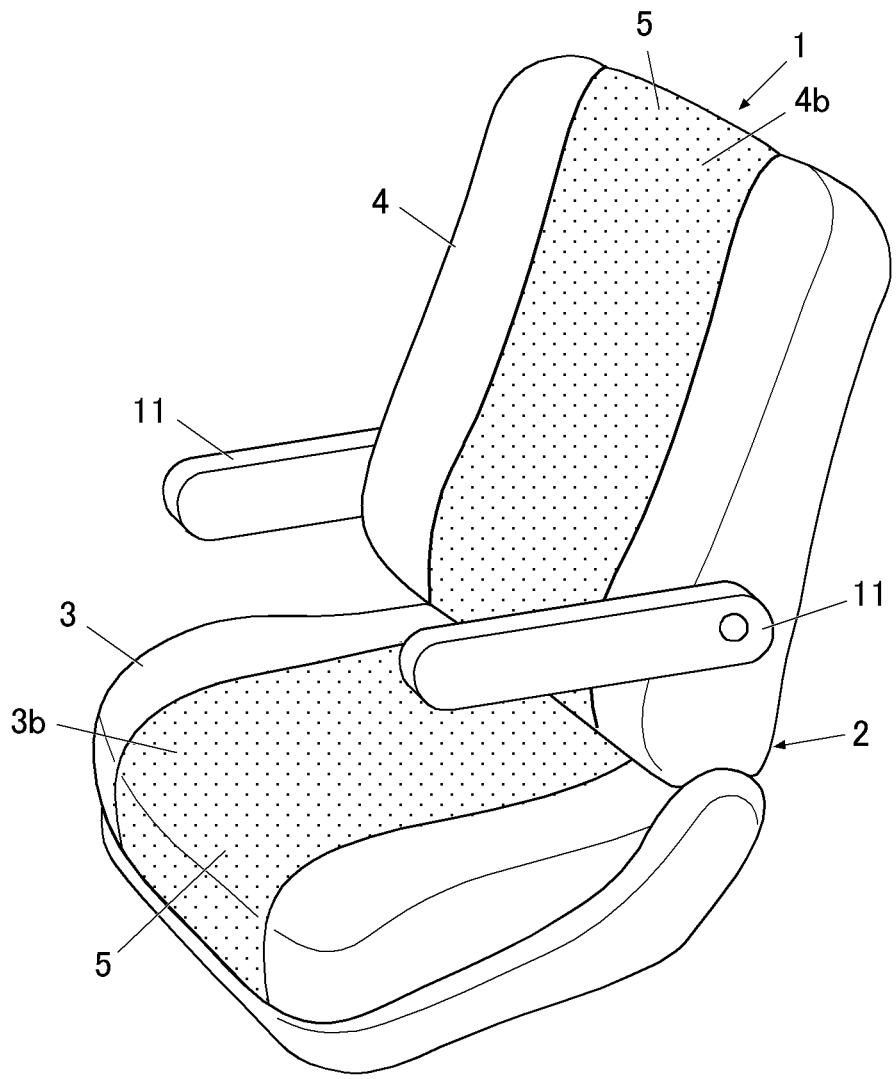
FIG. 5A illustrates an example of a seat having a covering material with punched holes.

In the example illustrated in FIG. 5A, punched holes 5 are formed in the covering material that forms the surface of the seat body 2 or the auxiliary supporters 11 to 15. The photoelectric pulse wave sensor 20 can emit light to the occupant P through the punched holes 5.

Figure 5B:
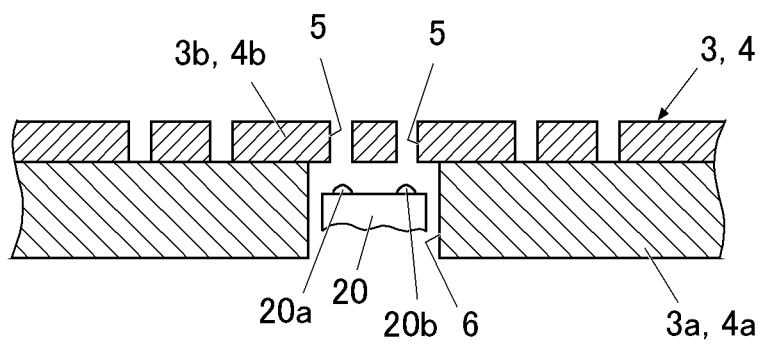
FIG. 5B illustrates installation of a biosensor in the seat in FIG. 5A.

As illustrated in FIG. 5B, an air path 6 is formed in the cushion pads 3a, 4a of the seat body 2 to allow air from a blower (not illustrated in the figure) to flow. The covering material 3b, 4b is provided to cover the cushion pads 3a, 4a in which the air path 6 is formed, so that the air flowing through the air path 6 can pass through the covering material 3b, 4b. By utilizing the punched holes 5 for ventilation, the photoelectric pulse wave sensor 20 can measure the pulse wave of the occupant P.

That is, to be exact, the photoelectric pulse wave sensor 20 is mostly masked, and a part (light emitter 20a, light receiver 20b) thereof is exposed through the punched holes 5 so that sensing is possible.

Figure 7:
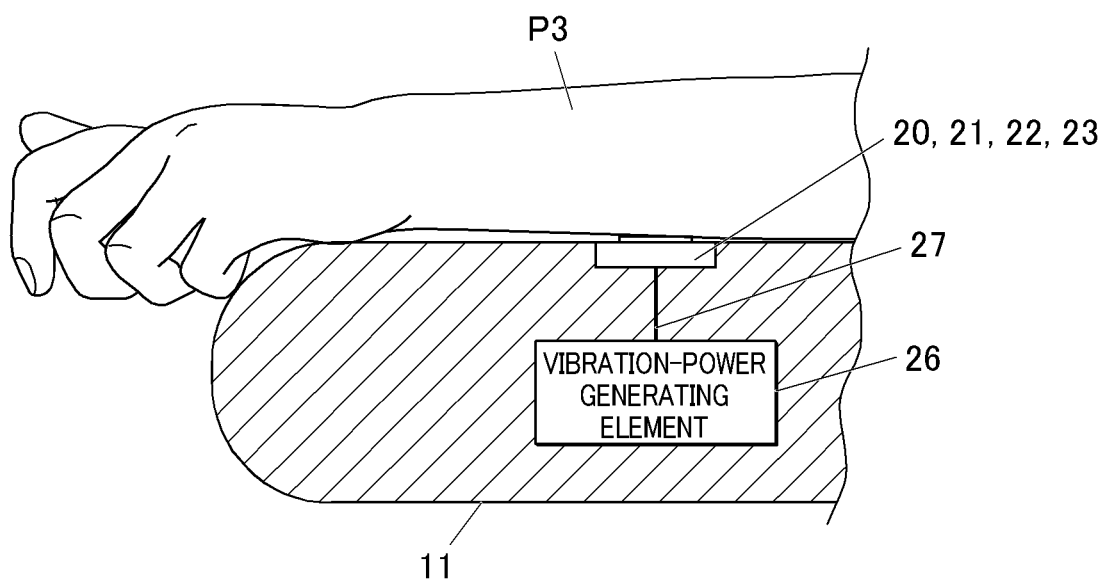
FIG. 7 illustrates the state in which a biosensor is connected to a vibration-powered generating element.

In the example illustrated in FIG. 6 and FIG. 7, the biosensor 20 to 23 is provided in the arm rest 11 in a completely exposed state. That is, the examples in FIG. 4, FIG. 5A and FIG. 5B explicitly illustrate that the biosensors 20 to 23 are readily exposable or exposed to an extent that allows sensing. However, the configuration is not limited thereto, and the biosensors 20 to 23 may be exposed on the surface of the seat 1.

The above-described plurality of biosensors 20 to 23 may be electrically powered by a battery of the vehicle V through communication/connection wires such as wire harnesses. Alternatively, the plurality of biosensors 20 to 23 may be electrically powered by using a vibration-powered generating element 26 that can generate electric power from vibration as illustrated in FIG. 7 and FIG. 8.

The vibration-powered generating element 26 may be provided in any position in the seat 1. In the example illustrated in FIG. 7, the biosensor 20 (21 to 23) and the vibration-powered generating element 26 are connected with each other by the communication/connection wire 27 such as a wire harness, and embedded in the arm rest 11 in a compactly assembled state (as a unit).

In the example illustrated in FIG. 7, the vibration-powered generating element 26 is embedded in the arm rest 11. However, the configuration is not limited thereto, and the vibration-powered generating element 26 may be provided in the seat body 2 or any of the other auxiliary supporters 12 to 15. When the biosensor 20 to 23 and the vibration-powered generating element 26 are assembled into a unit, the biosensor 20 (21 to 23) is disposed at the side closer to the body of the occupant P, i.e. at the surface side of the seat 1, so that the sensing by the biosensors 20 (21 to 23) is not interfered.

Figure 8:
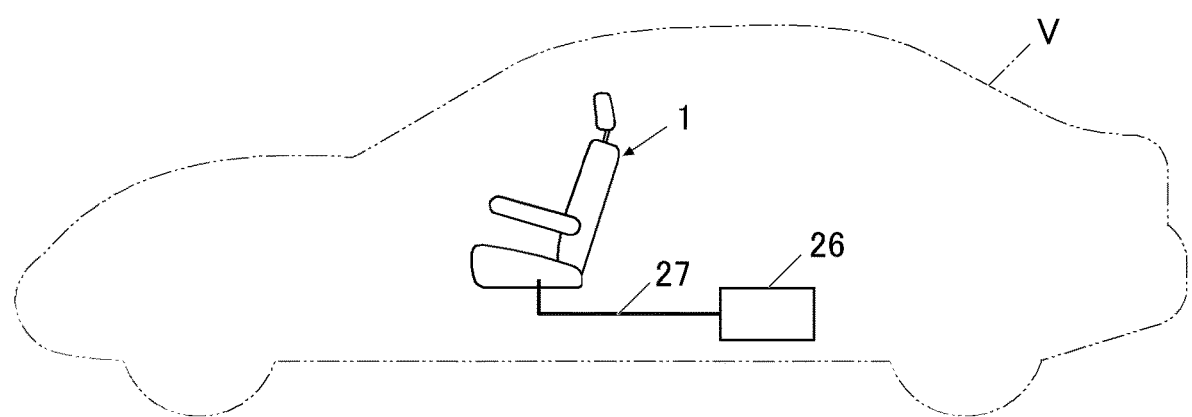
FIG. 8 illustrates the configuration in which the vibration-powered generating element is provided in a vehicle.

Instead of the seat 1, the vibration-powered generating element 26 may be provided in any part of the vehicle V as illustrated in FIG. 8. The seat 1 and/or the vehicle V may sometimes have a configuration that reduces vibration for providing more comfortable ride. In contrast, for example, an engine part and a chasse part such as suspensions are comparatively likely to vibrate. When the vibration-powered generating element 26 is provided in the vehicle V, the vibration-powered generating element 26 is preferably disposed in a part of the vehicle V that is comparatively likely to vibrate. Even when the vibration-powered generating element 26 is provided in the vehicle V, the biosensor 20 (21 to 23) and the vibration-powered generating element 26 are connected with each other by the communication/connection line 27 such as a wire harness.

For measurement of the health condition of the occupant P by using the biosensors 20 to 23 disposed in the seat body 2 and the plurality of auxiliary supporters 11 to 15 as described above, the reclined position as illustrated in FIG. 2 is optimal since measurement points can be set over the entire body. However, even the driving position in FIG. 1 has no problem since measurement points can be set over a wide area of the body depending on the type of the pulse wave sensors used. That is, the biological information can be obtained at a plurality of points in the body parts of the occupant P.

For example, in the case where the health condition of the occupant P who is a driver in a driving position as illustrated in FIG. 1 is measured while he/she is driving the vehicle, in response to detecting deterioration of the health condition of the occupant P, the driving controller V1 switches the mode from the manual driving mode to the autonomous driving mode to change the configuration of the seat 1 as illustrated in FIG. 2. Then, a more precise measurement may be made in this position. In this case, it is possible to obtain biological information of a different type from pulse wave data by using a biosensor 23 of a different type from the pulse wave sensors 20 to 22. This is preferred for making a precise measurement.

In the embodiment, the plurality of biosensors 20 to 23 for measuring the health condition of the occupant P are provided in the seat 1 for supporting the occupant P. The seat 1 includes: the seat body 2 that holds the occupant P; and the auxiliary supporters 11 to 15 for supporting respectively any of the parts P3 to P7 of the body of the occupant P except for the torso P1 and the thighs P2. Since at least one of the plurality of biosensors 20 to 23 is provided in the auxiliary supporters 11 to 15, it is possible to obtain biological information at a plurality of points that includes the body part P3 (P4 to P7) supported by the auxiliary supporter 11 (12 to 15) in which the biosensor 20 to 23 is provided as well as any of the other body parts P1 to P7. This can improve the accuracy in measuring the health condition of the occupant P.

Since the auxiliary supporters 11 to 15 include the arm rest 11 for supporting the arm P3 of the occupant P, it is possible to provide the biosensor 20 to 23 in the arm rest 11 and thereby to obtain the biological information at the arm P3. Since the front upper end of the arm rest 11 is the part where the biosensor 20 to 23 is installed, it is possible to provide the biosensor 20 to 23 in a position where it is likely to contact the arm P3. This facilitates obtainment of biological information at the arm P3.

Since the auxiliary supporters 11 to 15 includes the head rest 12 for supporting the head P4 of the occupant P, it is possible to provide the biosensor 20 to 23 in the head rest 12 and thereby to obtain the biological information at the head P4. Further, since the front side of the head rest 12 is the part where the biosensor 20 to 23 is installed, it is possible to provide the biosensor 20 to 23 in a position where it is likely to contact the head P4. This facilitates obtainment of the biological information at the head P4.

Since the auxiliary supporters 11 to 15 includes the neck rest 13 for supporting the neck P5 of the occupant P, it is possible to provide the biosensor 20 to 23 in the neck rest 13 and thereby to obtain the biological information at the neck P5. Further, since the front side of the neck rest 13 is the part where the biosensor 20 to 23 is installed, it is possible to provide the biosensor 20 to 23 in a position where it is likely to contact the neck P5. This facilitates obtainment of the biological information at the neck P5.

Since the auxiliary supporters 11 to 15 includes the ottoman 14 for supporting the legs P6 of the occupant P, it is possible to provide the biosensor 20 to 23 in the ottoman 14 and thereby to obtain the biological information at the legs P6. Further, since the left and right parts 14a, 14b of the ottoman 14 is the parts where the biosensor 20 to 23 is installed, it is possible to provide the biosensor 20 to 23 in a position where it is likely to contact the legs P6. This facilitates obtainment of the biological information at the legs P6.

Since the auxiliary supporters 11 to 15 includes the foot rest 15 for supporting the feet P7 of the occupant P, it is possible to provide the biosensor 20 to 23 in the foot rest 15 and thereby to obtain biological information at the feet P7. Further, since the left and right parts 15a, 15b of the foot rest 15 is the parts where the biosensor 20 to 23 is installed, it is possible to provide the biosensor 20 to 23 in a position where it is likely to contact the feet P7. This facilitates obtainment of the biological information at the feet P7.

Since the plurality of biosensors 20 to 23 includes a pulse wave sensor 20 to 22 for estimating the blood pressure of the occupant P, it is possible to measure the pulse wave of the occupant P at a plurality of points by using a plurality of biosensors 20 to 22 that are pulse wave sensors. This can improve the accuracy in estimating the blood pressure of the occupant P.

The pulse wave sensor is a photoelectric pulse wave sensor 20 that uses light to measure the pulse wave of the occupant. This is preferred for measuring the pulse wave at any of the body parts P1 to P7 that can be irradiated with light.

Since the photoelectric pulse wave sensor 20 is exposed on the covering materials 3b, 4b, 11a that form the surface of the seat body 2 or the auxiliary supporters 11 to 15, it is possible to prevent the covering materials 3b, 4b, 11a from blocking light. This can improve the accuracy of measurement by the photoelectric pulse wave sensor 20.

The pulse wave sensor is a piezoelectric pulse wave sensor 21 that measures the pulse wave of the occupant P by measuring a pressure wave on the body surface of the occupant P. This is preferred for measuring the pulse wave at any of the body parts P1 to P7 at which a pressure wave is measurable.

The pulse wave sensor is an electromagnetic pulse wave sensor 22 that measures the pulse wave of the occupant P by using electromagnetic waves. This allows measurement of the pulse wave of the occupant P even when the sensor is not in contact with the body of the occupant P.

Since at least one of the plurality of biosensors 20 to 23 is a biosensor 23 of a different type from the pulse wave sensors 20 to 22, it is possible to obtain other biological information and thereby to improve the accuracy in measuring the health condition of the occupant P The seat 1 is installed in the vehicle V that includes the operation controller V1 for switching between autonomous driving and manual driving, and the seat 1 is changeable to different forms between in autonomous driving and in manual driving. Even when the seat is changed to different forms between in autonomous driving and in manual driving, it is possible to make a measurement by the biosensors 20 to 23. Further, highly accurate measurement results are likely to be obtained by the plurality of biosensors 20 to 23 during autonomous driving, since it is easy to let the body to be supported by the auxiliary supporters 11 to 15.

On the other hand, to incorporate a sensing member such as the above-described biosensors into a seat, it is required to provide a wire harness that electrically connects the biosensor with an external device as well as a biosensor itself. However, depending on the position and the configuration of the biosensor and the wire harness provided in the seat, the functions of the seat may sometimes be impaired.

In the following description, regarding provision of a biosensor and a wire harness in a seat, an arrangement structure of a sensing member in the seat that does not impair the functions of the seat will be described.

The following description is based on an example in which a sensing member (a biosensor and a wire harness) is provided in a seat cushion or a seat back. However, the sensing member may be provided in a so-called auxiliary supporter of a seat such as a head rest, a neck rest, an arm rest, a foot rest or an ottoman. The present invention is also applicable to such cases in which the sensing member is formed in such an auxiliary supporter.

Figure 9:
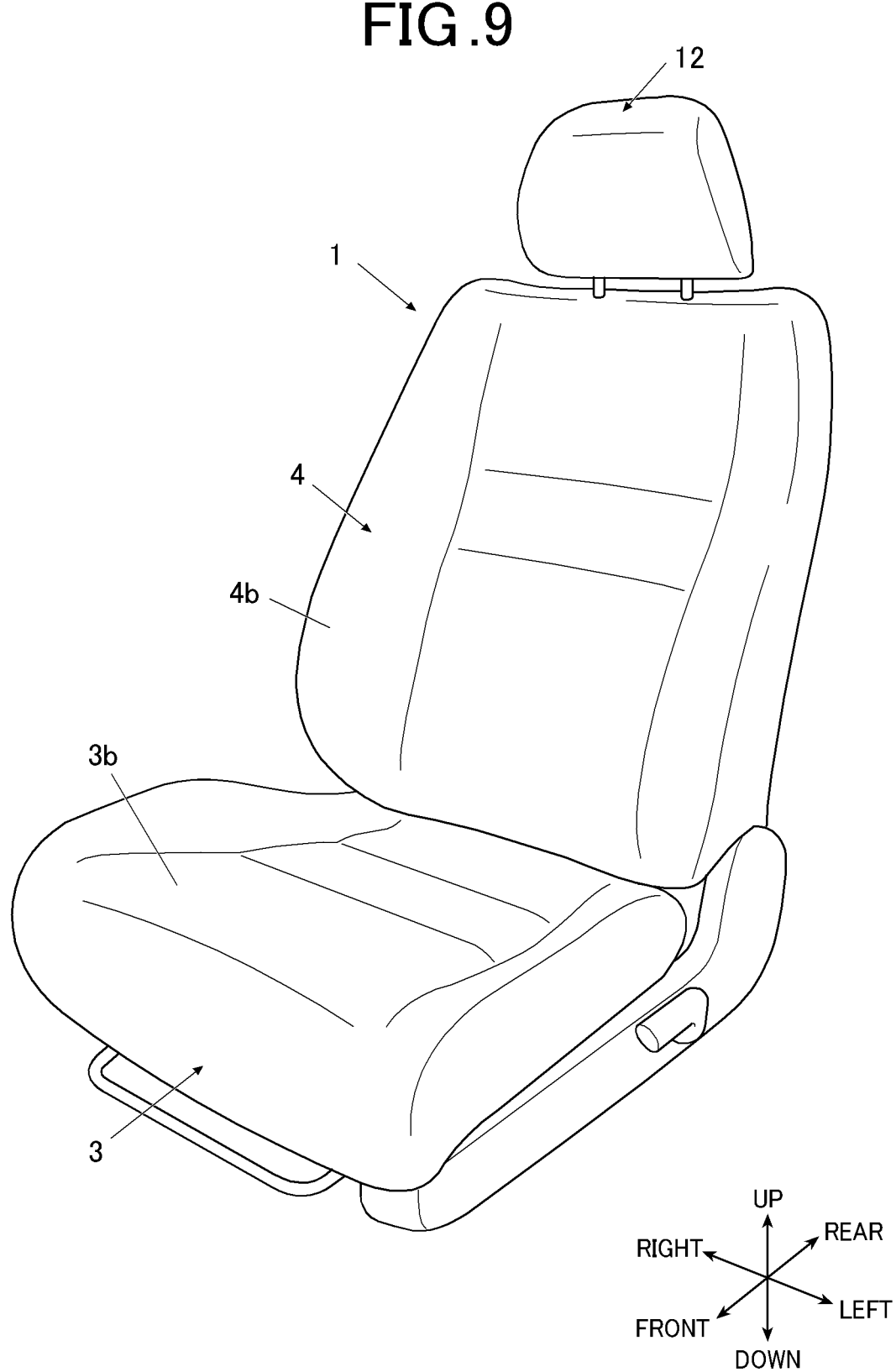
FIG. 9 is a perspective view of a seat.

The seat 1 illustrated in FIG. 9 is installed in a vehicle such as an automobile and is used for an occupant such as a driver to sit therein. As illustrated in FIG. 9, the seat 1 includes a seat cushion 3 for supporting the hip and the thighs of the occupant, a seat back 4 that is supported at the lower end by the seat cushion 3 to serve as a backrest, and a head rest 12 that is provided to the seat back 4 to support the head of the occupant. In addition, the seat 1 may further include an auxiliary supporter such as a neck rest, an arm rest, a foot rest and an ottoman.

Figure 10:
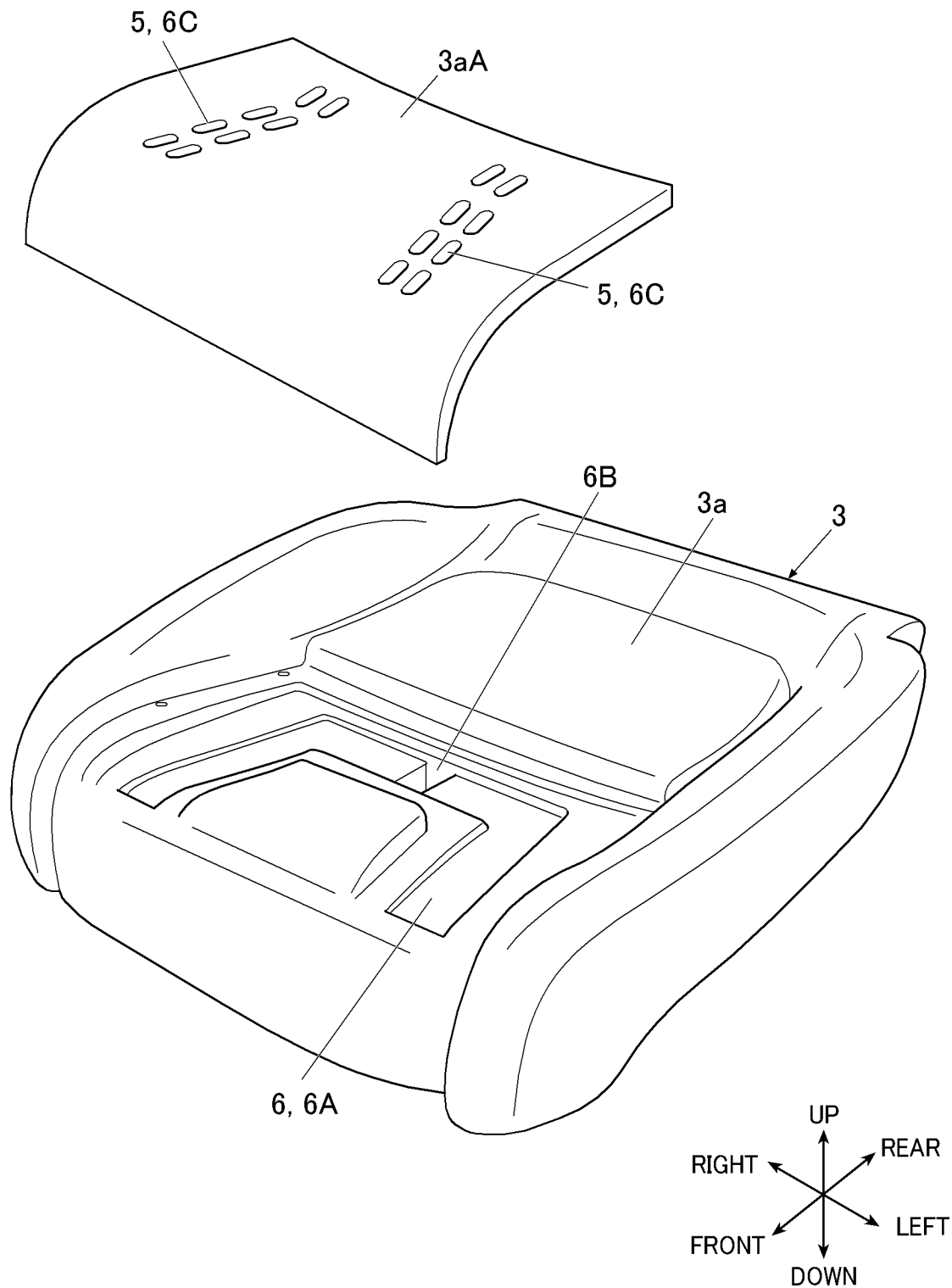
FIG. 10 is a perspective view illustrating an air path in a cushion pad of a seat cushion and an air outlet in a covering member.

As illustrated in FIG. 10, the seat cushion 3 mainly includes a seat cushion frame 7 as the frame (see FIG. 11 described later), a cushion pad 3a provided on the seat cushion frame 7, and a cover 3b covering the seat cushion frame 7 and the cushion pad 3a to form the surface of the seat (covering material 3b, not illustrated in FIG. 10, see FIG. 9).

In the seat cushion 3 of the embodiment, an air path 6 for air (warm air or cool air) is further provided between the cushion pad 3a and the cover 3b. Specifically, as illustrated in FIG. 10, a recess 6A as a part of the air path 6 is provided in the cushion pad 3a. Further, a recess (not illustrated in the figure) as the other part of the air path 6 is provided in a covering member 3aA in a position corresponding to the recess 6A. By fitting the covering member 3aA in a predetermined position of the cushion pad 3a, the air path 6 is formed.

A plurality of punched holes 5 are formed in the covering member 3aA, and the punched holes 5 serve as air outlets 6C of the air path 6. The cushion pad 3a including the covering member 3aA is covered with the cover 3b that is breathable at least at a part corresponding to the air outlets 6C.

Air blown by a blower 8 (described later, see FIG. 12 described later) flows through the through hole 6B to the air path 6, and the air flowing in the air path 6 is blown out toward the occupant through the air outlets 6C of the air path 6.

Figure 11:
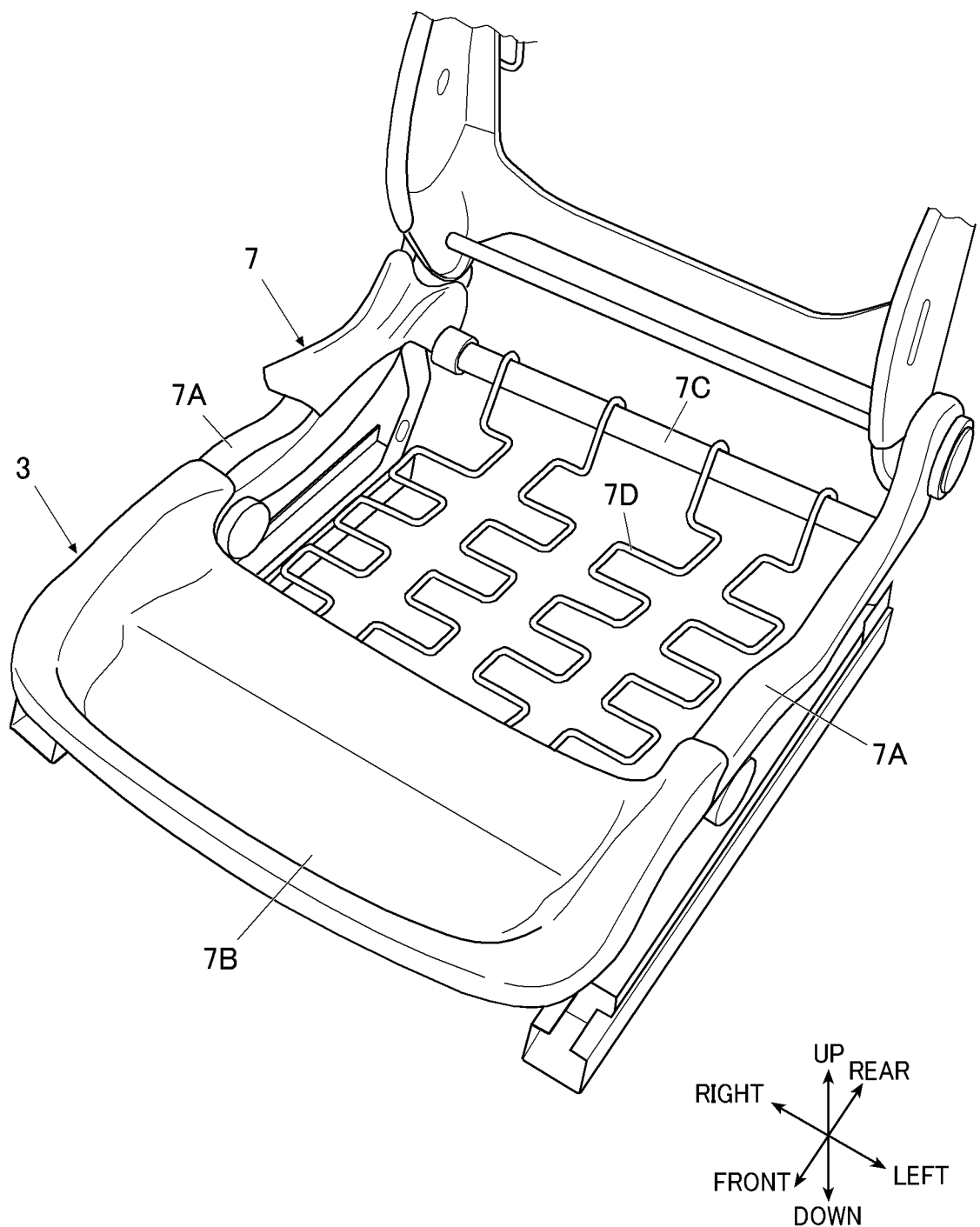
FIG. 11 is a perspective view of a seat cushion frame.

In the seat cushion 3 of the embodiment, the seat cushion frame 7 is disposed under the cushion pad 3a. As illustrated in FIG. 11, the seat cushion frame 7 mainly includes a pair of right and left side frames 7A, a pan frame 7B coupling the front parts of the side frames 7A to each other, coupling members 7C coupling respectively the front ends and the rear ends of the side frames 7A with each other (see FIG. 12 described later for a front-end coupling member 7C).

Between the pan frame 7B and a rear-end coupling member 7C, a plurality of zig-zag springs 7D are provided.

Figure 12:
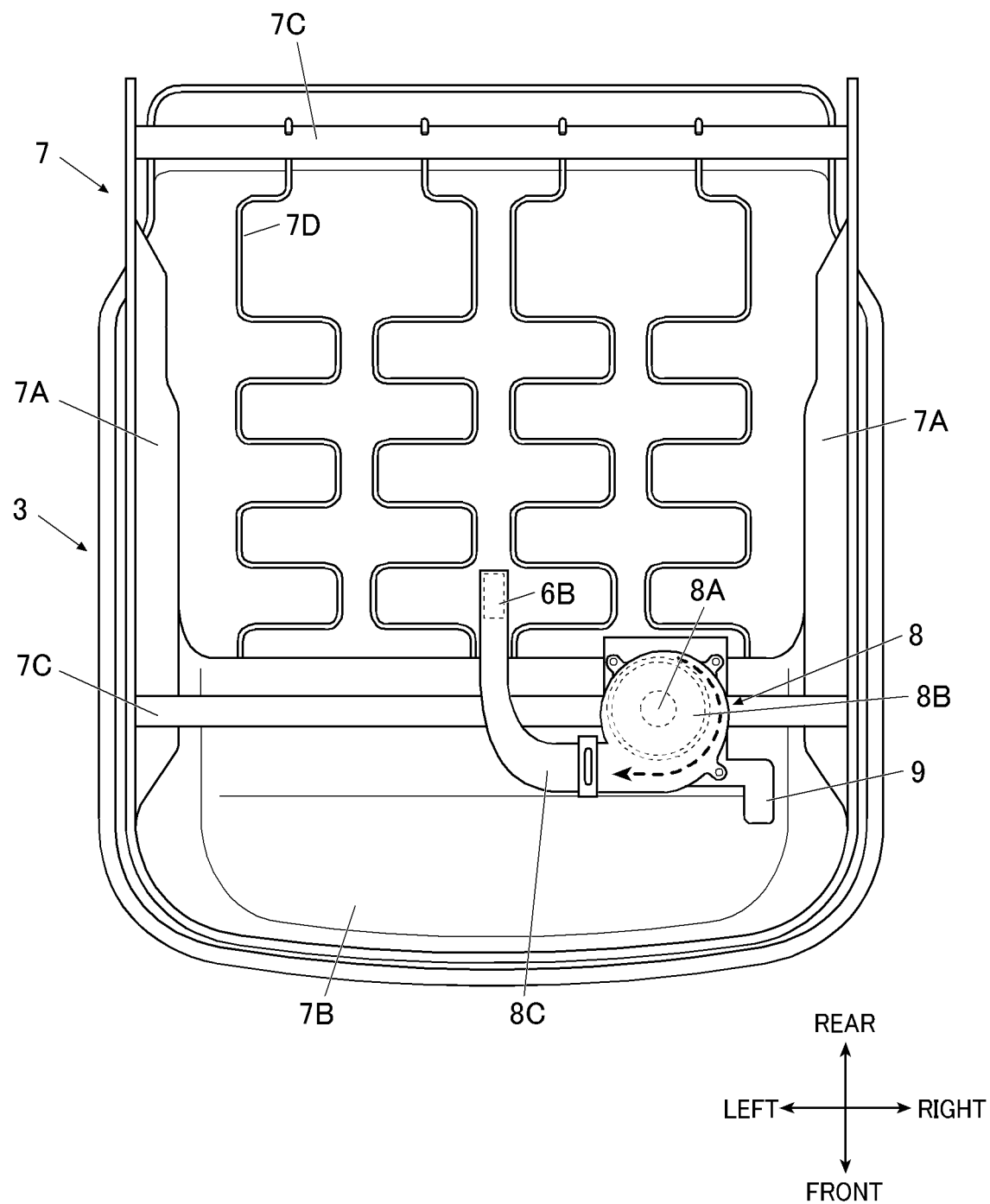
FIG. 12 is a view from below of the seat cushion.

FIG. 12 is a view from below of the seat cushion 3. As illustrated in FIG. 12, a blower 8, and an attachment member 9 that fixes the blower 8 to the pan frame 7B are provided below the pan frame 7B.

The blower 8 includes a motor 8A, a fan 8B, a duct 8C and the like, and the duct 8C is connected to the above-described through hole 6B of the air path 6. The blower 8 is configured to suck air through an inlet (not illustrated in the figure) by rotation of the fan 8B and to blow the air toward the air path 6 through the duct 8C and the through hole 6B.

Although not illustrated in detail in the figures, the seat back 4 (see FIG. 9) has the same configuration as the above-described seat cushion 3. A cover 4b (covering material 4b) of the seat back 4 has a plurality of air outlets 6C for the air path 6, and air flowing through the air path 6 is blown toward the occupant (not illustrated in the figure) through the air outlets 6C.

The seat cushion 3 and the seat back 4 may include respective blowers 8. Alternatively, a blower 8 may be provided in one of the seat cushion 3 and the seat back 4, and the blower 8 may be configured to send air also to the other air path 6. Further, the seat 1 may include an additional structure such as a heater.

Figure 13:
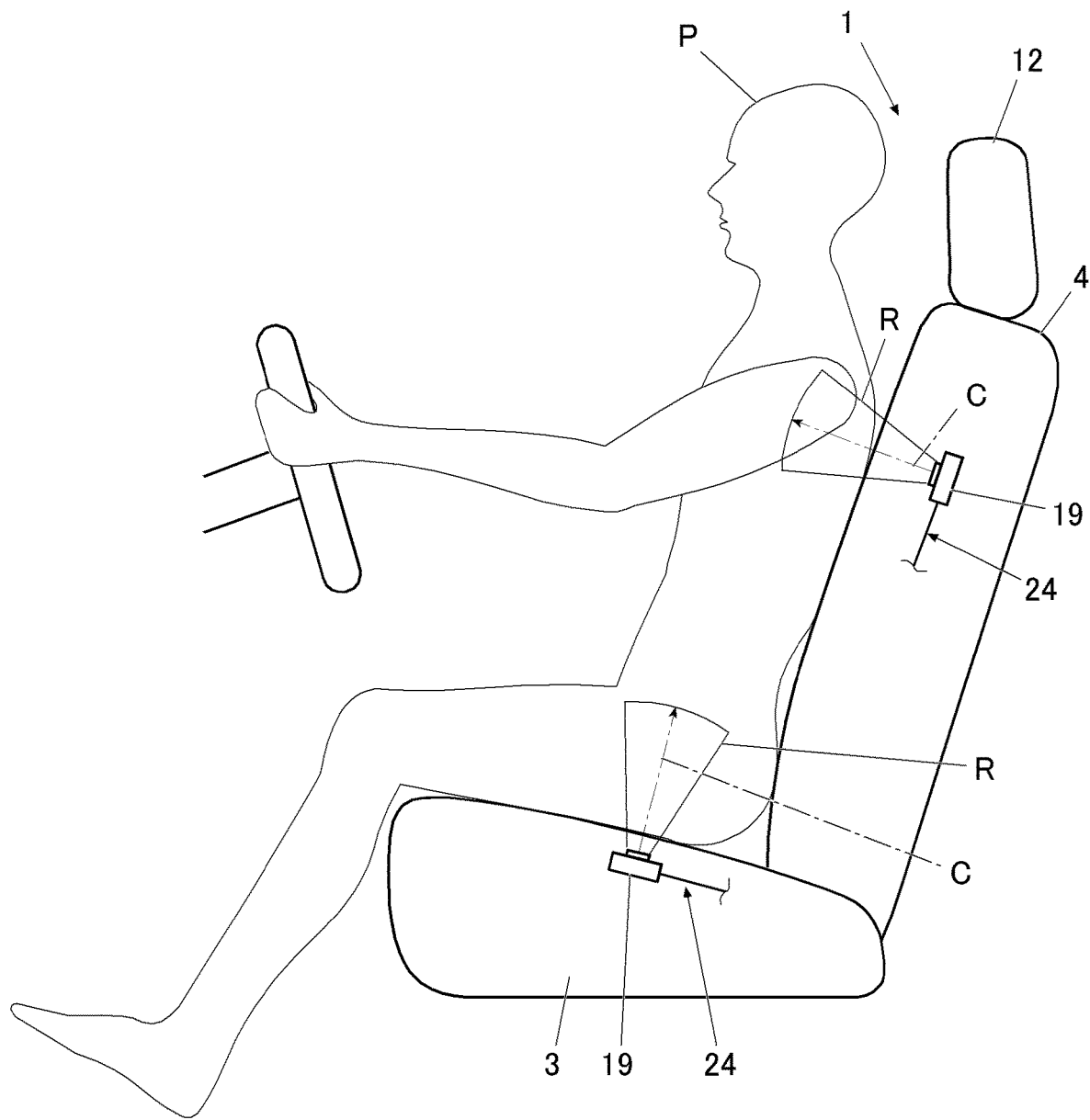
FIG. 13 illustrates an arrangement example of biosensors and wire harnesses in the seat.

As illustrated in FIG. 13, biosensors 19 are provided in the seat 1.

In the following description, the biosensors are not specified such as the above-described biosensors 20 to 23 (the photoelectric pulse wave sensor 20, the piezoelectric pulse wave sensor 21, the electromagnetic pulse wave sensor 22, and the biosensor 23 of a different type from the pulse wave sensors 20 to 22) but correctively referred to as biosensors 19.

For example, each of the biosensors 19 of the embodiment is provided to measure the blood flow condition of a subject person (occupant P), which can measure the blood flow at a point opposed to the skin surface in the measurement area. The biosensor 19 of the embodiment is a non-contact sensor that detects the biological information of the occupant P by using an electromagnetic wave and an ultrasound. The biosensor 19 is electrically connected to an external device by a wire harness 24.

The biosensor 19 is electrically powered by an external power supply via the wire harness 24 and transmits detected biological information to the external device via the wire harness 24.

The biosensor 19 and the wire harness 24 are collectively referred to as a sensing member. FIG. 13 illustrates an example in which two biosensors 19 and two wire harnesses 24 (i.e. two sensing members) are provided in the seat 1. Instead, only a single sensing member may be provided in the seat 1, or three or more sensing members may be provided.

By disposing the biosensors 19 at at least two points of the seat 1 away from each other, for example in the seat cushion 3 and the seat back 4 (or an auxiliary supporter or the like such as the head rest 12) as illustrated in FIG. 13, it is possible to detect the biological information from at least two points of the human body. This can improve the accuracy in calculating a human health condition from the detected biological information compared to a case in which only a single biosensor 19 is used.

The biosensors 19 may include a sensor that detects human biological information by emitting an electromagnetic wave.

As used herein, an electromagnetic wave means an electromagnetic wave in a broad sense, including a radio wave of approximately 100 MHz and a microwave as well as infrared light, visible light, ultraviolet light, X ray, and the like. A suitable electromagnetic wave is used within the range in which the human body is not harmed.

Such electromagnetic waves have a characteristic of unlikely penetrating through various metals such as iron, copper, and aluminum. For this reason, each biosensor 19 of the embodiment is disposed in the seat 1 in a position aside from members that prevent or may prevent penetration of electromagnetic waves.

Specifically, the biosensor 19 is desirably disposed in a position in which members that prevent or may prevent penetration of electromagnetic waves do not mask the irradiation center C of an electromagnetic wave emitted from the biosensor 19, and such members overlap the irradiation area R of the electromagnetic wave as little as possible.

The biosensors 19 and the wire harnesses 24, i.e. the sensing members, may be disposed basically anywhere in the seat cushion 3 and the seat back 4 (and the auxiliary supporters such as the head rest 12) of the seat 1 as long as the sensing members neither disturb the occupant P, nor interfere attaching the members of the seat, nor impair the various functions of the seat. Further, the wire harnesses connected to the biosensors 19 may also be disposed basically anywhere in the seat 1 as long as the above requirements such as not disturbing the occupant P are satisfied.

That is, in the present invention, the sensing members may be disposed basically anywhere in the seat 1.

However, as described above, depending on the position in the seat 1 and the configuration of the sensing members, the functions of the seat 1 may sometimes be impaired.

For example, in the embodiment, the seat 1 has the air path 6 (see FIG. 10), and has a warming or cooling function that is achieved by sending air such as warm air or cool air to the air path 6 by means of the blower 8 (see FIG. 12) and blowing out the air toward the occupant P through the air outlets 6C.

In such cases, when a sensing member, i.e. a biosensor 19 and a wire harness 24, is disposed in the air path 6 of the seat 1, the biosensor 19 and the wire harness 24 may block air flow in the air path 6.

Such blockage of air flow in the air path 6 by the biosensor 19 and the wire harness 24 causes a turbulence in the air path 6 and resultant pressure loss of the air. This reduces the amount of air to be blown through the air outlets 6C of the covers 3b, 4b of the seat 1. As a result, the amount of warm or cool air to be blown out through the air outlets 6C may be unfavorably reduced to a level lower than intended, or warm or cool air may not be blown out.

To cope with the problem, in the embodiment, each of the sensing members such as biosensors 19 and the wire harnesses 24 is disposed in such a position that they do not disrupt air flow in the air path 6 of the seat 1 or in such a configuration that they do not disrupt air flow in the air path 6.

Figure 14A:
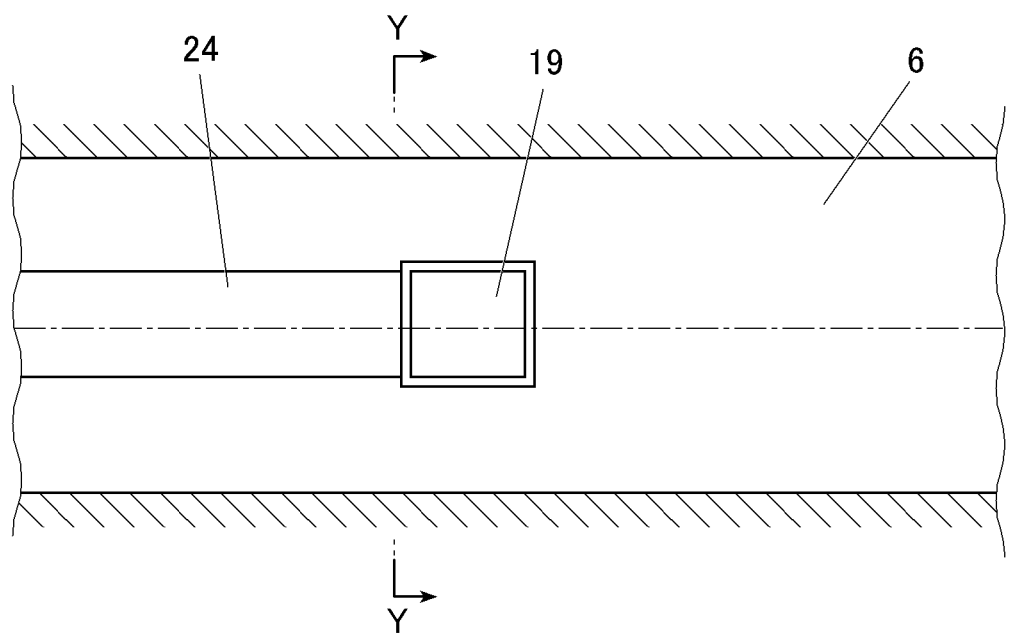
FIG. 14A is a cross-sectional view illustrating a configuration in which a biosensor and a wire harness are disposed in a position including the center of the air path.
Figure 14B:
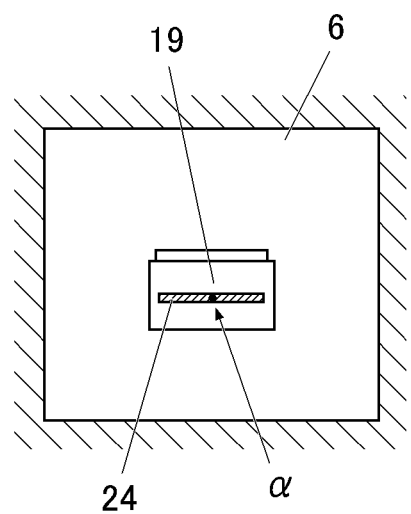
FIG. 14B is a cross-sectional view taken along the line Y-Y in FIG. 14A.

According to a study by the present inventors on the arrangement of the biosensor 19 and the wire harness 24 in the air path 6, when the biosensor 19 and the wire harness 24 is disposed in a position including the center a of the air path 6 as illustrated in FIG. 14A and FIG. 14B, the biosensor 19 and the wire harness 24 cause a turbulence in the air path 6.

To cope with the problem, in the embodiment, when the sensing member such as the biosensor 19 and the wire harness 24 is provided in the air path 6 of the seat 1, the sensing member such as the biosensor 19 and the wire harness 24 is disposed in a position off the center α of the air path 6.

FIG. 14A, and FIG. 15, FIG. 17A, FIG. 18, FIG. 19A and FIG. 19B, which are described later, are cross-sectional views taken in the extending direction of the air path 6, while FIG. 14B, and FIG. 16A, FIG. 16B and FIG. 17B, which are described later, are cross-sectional views taken in the direction perpendicular to the extending direction of the air path 6.

Since the sensing member is disposed in a position off the center α of the air path 6, the sensing member such as the biosensor 19 and the wire harness 24 is less likely to disrupt air flow in the air path 6 of the seat 1 and cause a turbulence in the air path 6. Accordingly, pressure loss of the air is not caused, and it becomes easier to prevent reduction of the amount of air blown through the air outlets 6C of the cover 3b, 4b of the seat 1.

As a result, even though the sensing member such as the biosensor 19 and the wire harness 24 is disposed in the air path 6 of the seat 1, the warming and cooling function of the seat 1 is less likely to be impaired. Further, it becomes easier to allow the seat 1 to fulfill the warming and cooling function. In other words, the sensing members are less likely to impair the function.

Figure 15:
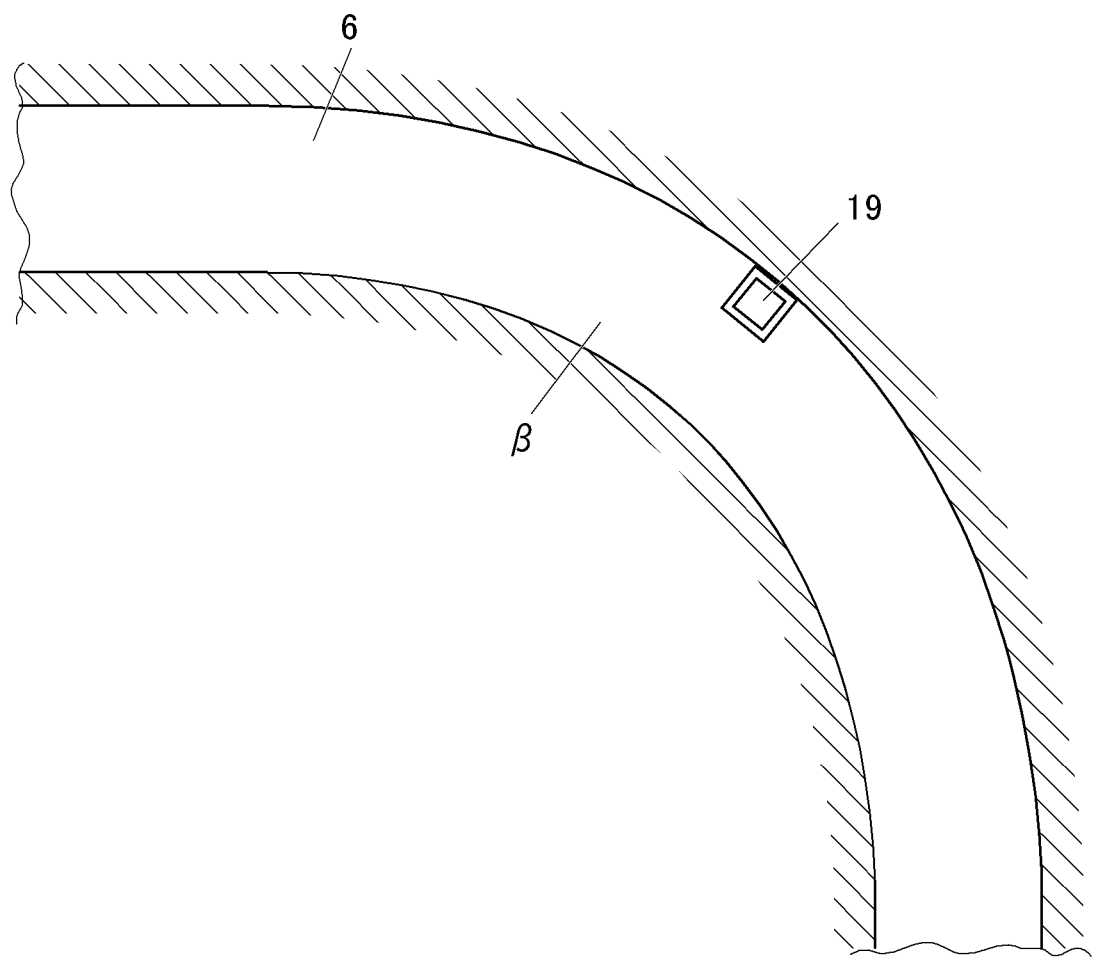
FIG. 15 is a cross-sectional view illustrating a configuration in which a biosensor is disposed in a curved portion of the air path.

In a curved portion of the air path 6, a turbulence of air is likely to be caused inherently since the direction of the flowing air is changed at the portion. When the sensing member including the biosensor 19 is disposed at a curved portion β of the air path 6 as illustrated in FIG. 15, the biosensor 19 and the like disturbs the air flow that is inherently prone to cause a turbulence. This may sometimes results in a turbulence in the air path 6.

To avoid this, it is desired not to provide the sensing members including the biosensors 19 at the curved portion β of the air path 6.

As illustrated in FIG. 14A, FIG. 14B and FIG. 15, the following description is based on an example in which the sensing members such as the biosensors 19 and the wire harnesses 24 are mainly disposed in the air path 6 of the cushion pad 3a of the seat 1. Hereinafter, the term cushion pad 3a includes cushion pads of the seat back 4 and the auxiliary supporters and the like as well as the cushion pad of the seat cushion 3. However, it is needless to say that, for example, a hole and/or through hole may be formed in the cushion pad 3a and the like in addition to the air path 6, and each of the biosensors 19, the wire harnesses 24 and the like may be disposed in the hole and/or through hole.

Each of the sensing members such as the biosensors 19 and the wire harnesses 24 may be disposed in the blower 8 and/or the duct 8C (see FIG. 12) for supplying air to the air path 6. For example, a biosensor 19 that cannot sufficiently fulfill the sensor function at low temperature may be disposed in the blower 8 or the duct 8C. This makes easier for the biosensor 19 to fulfill the function since the biosensor 19 is heated when the blower 8 sends warm air to the air path 6.

When the biosensors 19 is disposed in the blower 8 or the like, necessary measures are taken to allow electromagnetic waves or the like emitted from the biosensor 19 to reach the occupant P. Such measures include providing a hole above the biosensor 19 in the pan frame 7B or the like and making the pan frame 7B from a material that transmits electromagnetic waves or the like.

To the contrary, when a biosensor 19 and a wire harness 24 are vulnerable to high temperature, it is possible not to dispose the sensing member such as the biosensor 19 and the wire harness 24 near the blower 8 and the duct 8C that are sometimes heated to a high temperature. In this configuration, the biosensor 19 and the wire harness 24 are not heated by the heated blower 8 and the duct 8C. This makes easier for the biosensor 19 to fulfill the function since the biosensor 19 and the like are less likely to be heated to a high temperature.

Figure 16A:
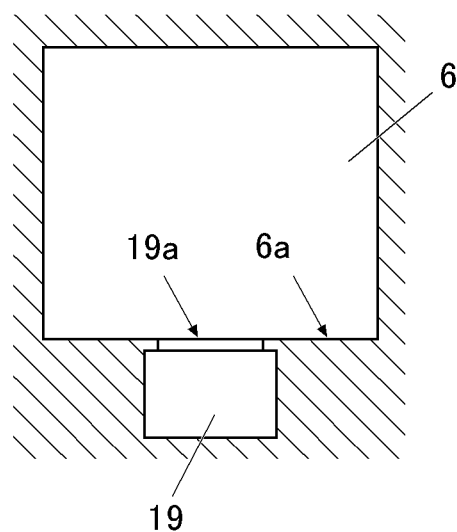
FIG. 16A is a cross-sectional view illustrating a configuration in which a biosensor is embedded flush with the wall surface of the air path.

When each of the sensing members such as the biosensors 19 and the wire harnesses 24 is disposed in the air path 6 of the cushion pad 3a of the seat 1, it is possible to embed the biosensor 19 in the wall 6a of the air path 6 so that surface 19a exposed to the air path 6 is flush with the wall 6a of the air path 6, for example, as illustrated in FIG. 16A.

When the surface 19a of the biosensor 19 forms a protrusion or a recess on the wall 6a of the air path 6, the protrusion or recess may cause a turbulence in the air path 6. In contrast, when the surface 19a of the biosensor 19 is flush with the wall 6a of the air path 6 as in the above-described configuration, air flows smoothly in the air path 6. In the above-described configuration, the biosensor 19 is provided in a manner that does not disrupt air flow in the air path 6. This reduces the occurrence of a turbulence in the air path 6, and air flow in the air path 6 is less likely to be disrupted by the biosensor 19.

Figure 16B:
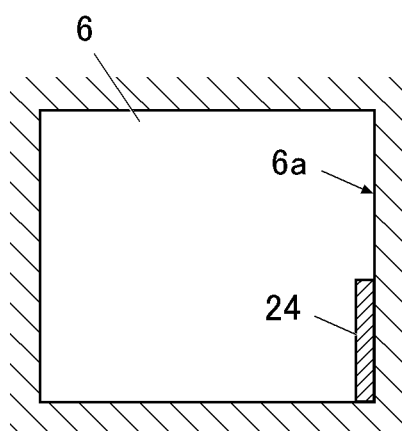
FIG. 16B is a cross-sectional view illustrating a configuration in which a wire harness is disposed along the wall surface of the air path.

When each of the wire harnesses 24 is disposed in the air path 6, the wire harness 24 may be disposed along the wall 6a of the air path 6, for example, as illustrated in FIG. 16B. In this configuration, the air in the air path 6 flow smoothly along the wire harness 24, and it therefore is possible to provide the wire harness 24 in a manner that does not disrupt air flow in the air path 6. This can reduce the occurrence of a turbulence in the air path 6, and the wire harness 24 is less likely to disrupt the air flow in the air path 6.

Figure 17A:
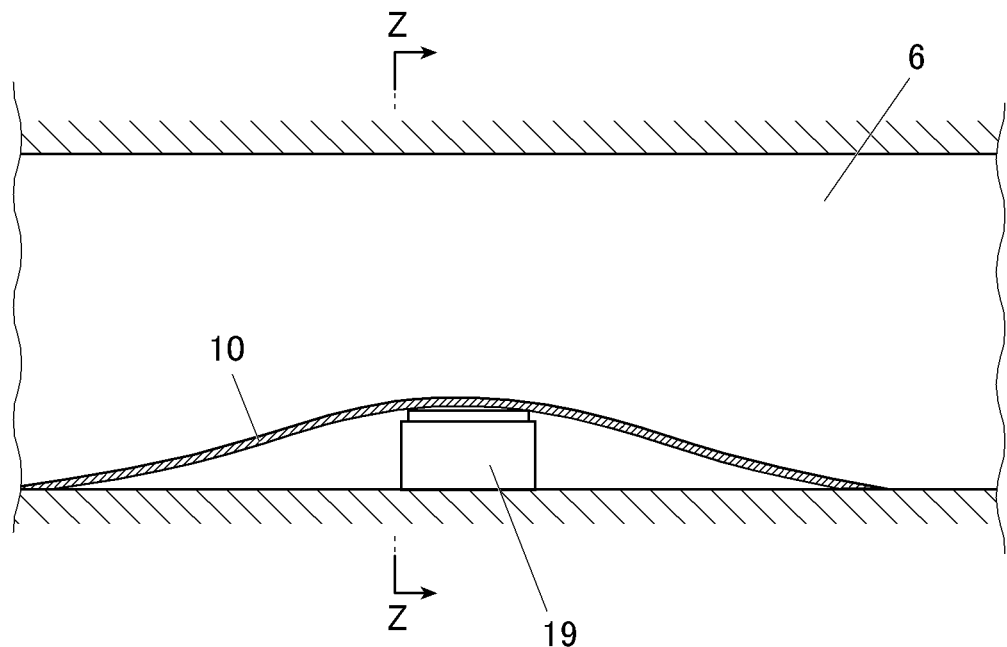
FIG. 17A is a cross-sectional view illustrating a configuration in which a biosensor with a guide face is disposed in the air path.
Figure 17B:
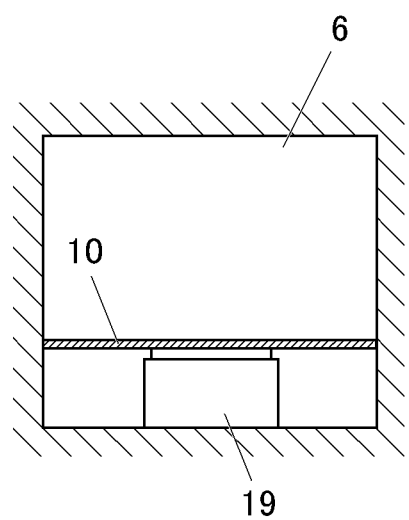
FIG. 17B is a cross-sectional view taken along the line Z-Z in FIG. 17A.

When each of the sensing members such as the biosensors 19 and the wire harnesses 24 is disposed in the air path 6, the biosensor 19 may have a guide face 10 that guides the air in the air path 6 so that the air in the air path 6 is deviated from the biosensor 19 and flows smoothly, for example, as illustrated in FIG. 17A and FIG. 17B.

With the guide face 10, it is possible to provide the biosensor 19 in a manner that deviates air flow in the air path 6 from the biosensor 19. The guide face 10 allows the air to flow smoothly and prevents the biosensor 19 from disrupting air flow in the air path 6. Accordingly, this configuration can reduce the occurrence of a turbulence in the air path 6 even when the biosensor 19 and the like are provided in the air path 6. Therefore, the air flow in the air path 6 is less likely to be disrupted by the biosensor 19 and the like.

When the guide face 10 is disposed over the sensor surface of the biosensor 19 as illustrated in FIG. 17A and FIG. 17B, the guide face 10 may impair the sensor function of the biosensor 19. For example, this may occur when the biosensor 19 is of the type that emits electromagnetic waves or the like and the guide face 10 is made of a material that does not transmit electromagnetic waves such as metals. To avoid this, the guide face 10 is made of a material that transmits electromagnetic waves emitted from the biosensors 19, such as resin.

When the biosensor 19 is a photoelectric sensor, the guide face 10 can be made of a transparent material that transmits light emitted from the biosensor 19.

As long as the biosensor 19 with the guide face 10 as illustrated in FIG. 17A and FIG. 17B do not cause a turbulence of the air flowing in the air path 6 even when the biosensor 19 is disposed at the curved portion β of the air path 6 (see FIG. 15), it is also possible to dispose the biosensor 19 with the guide face 10 at the curved portion β of the air path 6.

Figure 18:
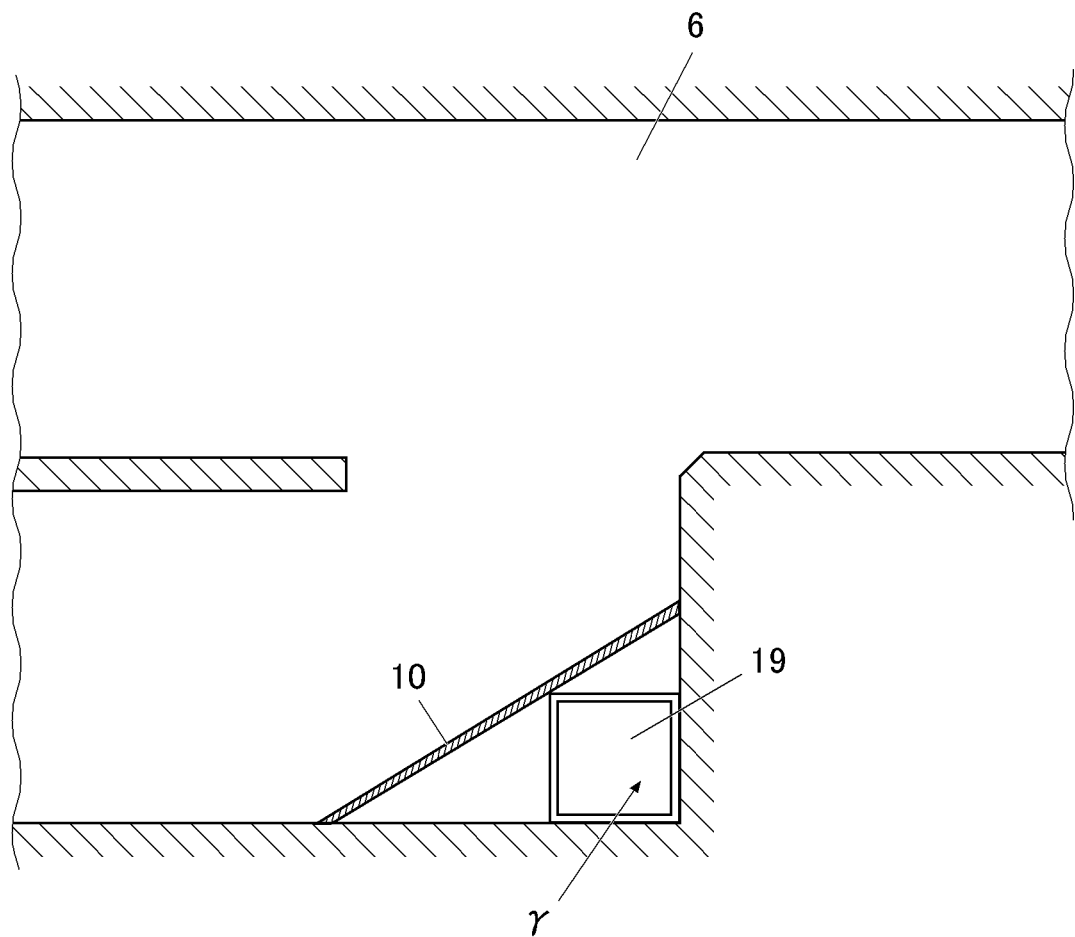
FIG. 18 is a cross-sectional view illustrating a configuration in which a biosensor with a guide face is disposed at a corner of the air path.

The above-described guide face 10 can be used also when the biosensor 19 and the like are disposed at a corner γ of the air path 6, for example, as illustrated in FIG. 18.

In this configuration, the guide face 10 isolates the biosensor 19 at the corner γ of the air path 6 from air flow at the corner γ of the air path 6, and the guide face 10 thereby allows air to flow smoothly. This can reduce the occurrence of a turbulence in the air path 6 and make the biosensor 19 and the like less likely to disrupt air flow in the air path 6 even when the biosensor 19 and the like are provided at the corner γ of the air path 6.

FIG. 18 illustrates an example in which the guide face 10 is formed in a flat shape. However, the guide face 10 may be formed in a curved shape. This also applies to the example illustrated in FIG. 19B, which will be described later.

As described above, in the embodiment, the covering member 3aA (see FIG. 10) of the seat 1 has the air outlets 6C for blowing out air in the air path 6 toward the occupant P. When each of the biosensors 19 emits electromagnetic waves to the occupant P for sensing, the air outlets 6C may be configured such that the electromagnetic waves are emitted to the occupant P through the air outlets 6C. This configuration are likely to improve the emission efficiency of electromagnetic waves to the occupant P and makes it easier to improve the sensitivity of the biosensor 19 since electromagnetic waves are not disrupted at the air outlets 6C.

For this reason, when the biosensor 19 is provided in the air path 6 of the cushion pad 3a of the seat 1, the biosensor 19 is preferably disposed in a position facing the air outlets 6C.

Figure 19A:
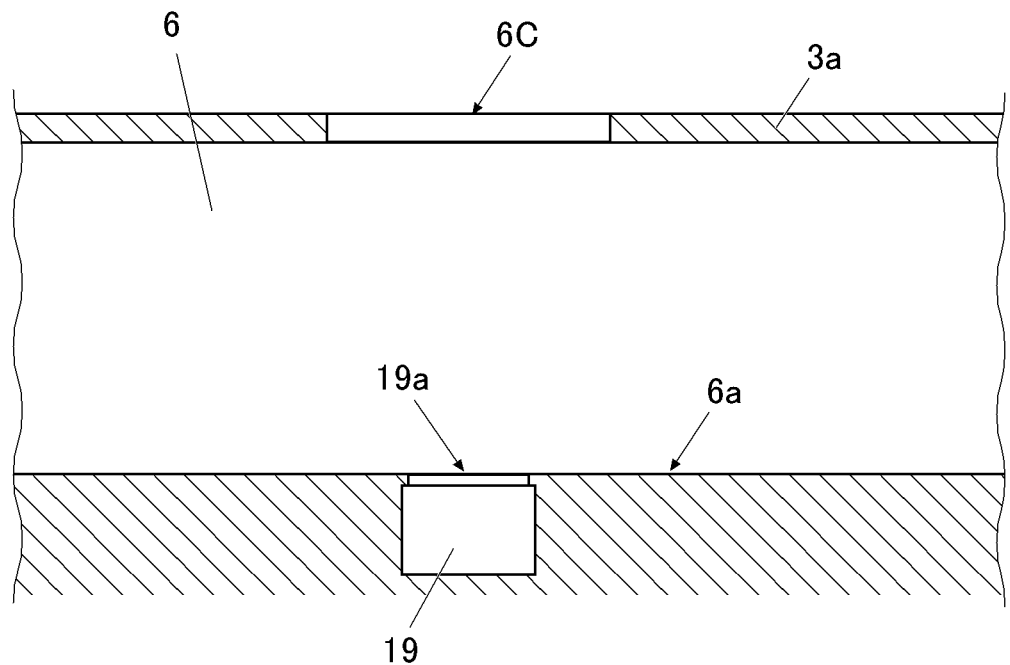
FIG. 19A is a cross-sectional view illustrating a configuration in which a biosensor is disposed opposite the air outlet and embedded flush with the wall surface of the air path.

In this case, for example, it is possible to employ the configuration as illustrated in FIG. 16A. The biosensor 19 may be embedded in the wall 6a of the air path 6 in an area facing the air outlets 6C so that the face 19a of the biosensor 19 is flush with the wall 6a of the air path 6 as illustrated in FIG. 19A.

Figure 19B:
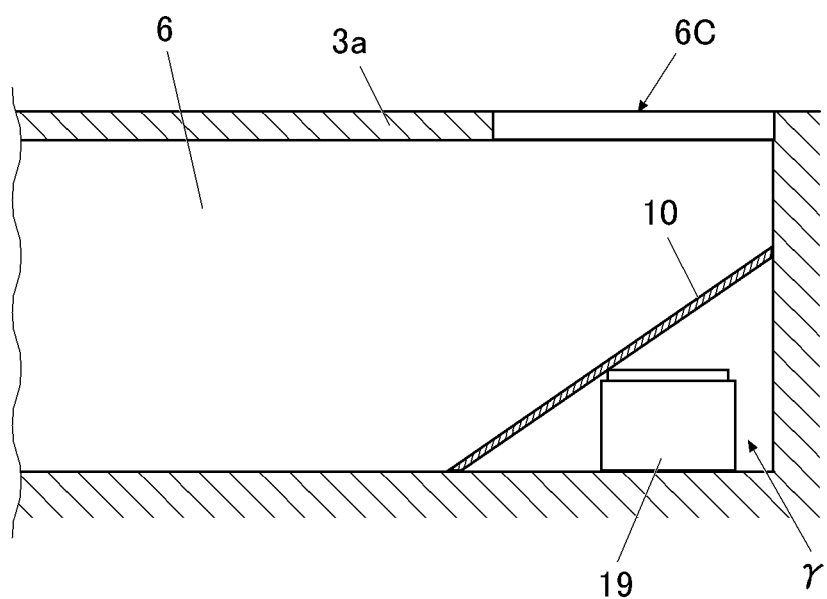
FIG. 19B is a cross-sectional view illustrating a configuration in which a biosensor with a guide face is disposed opposite the air outlet and at a corner of the air path.

Further, although not illustrated in the figures, for example, it is also possible to employ the configuration as illustrated in FIG. 17A and FIG. 17B. The biosensor 19 disposed in a position facing the air outlets 6C may be covered with the guide face 10. Further, when the air outlets 6C are formed at the corner γ of the air path 6 as illustrated in FIG. 19B, for example, it is possible to employ the configuration as illustrated in FIG. 18. The biosensor 19 disposed at the corner γ of the air path 6 may be covered with the guide face 10 so that the biosensor 19 is isolated from air flow from the air path 6 toward the air outlets 6C.

Any of the above-described configurations reduces the occurrence of a turbulence in the air path 6 due to the biosensor 19, and the biosensor 19 is less likely to disrupt the air flow in the air path 6.

As described above, in the arrangement structure of the sensing members (biosensors 19 and the wire harnesses 24) in the seat 1 according to the embodiment, the sensing members are disposed in a such position that they do not disrupt air flow in the air path or in a such configuration that they do not disrupt air flow in the air path 6.

This prevents the sensing members from causing a turbulence in the air path 6, and the sensing members are less likely to disrupt air flow in the air path 6.

The seat 1 may have a warming and cooling function that is achieved by blowing out warm or cool air from the air outlets 6C toward the occupant P to warm or cool the occupant P as in the embodiment. In such cases, even when the sensing members such as the biosensors 19 and the wire harnesses 24 are provided in the seat 1, the functions of the seat 1 such as the warming and cooling function are less likely to be impaired. Further, it becomes easier to allow the seat 1 to fulfill its functions.

The present invention is not limited to the above-described embodiment, and suitable changes can be made without departing from the features of the present invention.

For example, as described above (see FIG. 8), electric power may be supplied from the vibration-powered generating element 26 to each of the biosensors 19 in the seat 1 via the communication/connection wires 27 (wire harnesses 24).

Then, for example, each of the wire harnesses 24 connected to the vibration-powered generating element 26 is disposed to run through the through hole 6B (see FIG. 10), the air path 6 and the like in the seat 1 and to be connected to the biosensor 19 provided in the seat 1. It is possible to connect the biosensor 19 to the vibration-powered generating element 26 by the wire harness 24, and to supply electric power from the vibration-powered generating element 26 to the biosensor 19 through the wire harness 24 to drive the biosensor 19.

In this regard, the arrangement structure of the sensing members in the seat as illustrated in the above embodiment may be applied to the arrangement of the biosensors 19 and the wire harnesses 24. As a result, even when the biosensors 19 and the wire harnesses 24 are disposed in the seat 1, the functions of the seat 1 such as the warming and cooling function are less likely to be impaired. Further, it becomes easier to allow the seat 1 to fulfill the functions.

On the other hand, regarding techniques of understanding the health condition of a driver that involve detecting and estimating the biological information such as the blood flow and the blood pressure based on measurement results such as the pulse wave by non-contact blood flow sensors embedded in the sitting surface and the seatback surface of a seat, techniques described in JP 2017-060584A and JP 2016-159081A are also known in the art in addition to the above-described technique described in Patent Document 1.

Sensors and antennas described in these documents are all provided inside a seat and configured to indirectly measure the biological information without directly contacting the occupant. Accordingly, detected values vary depending on, for example, the cloth and the like of the occupant. This can results in a different determination on whether an abnormality has occurred.

For example, even when an occupant having high blood pressure is seated in the seat, the sensors may erroneously detect a lower blood pressure than reality, and the abnormality of the occupant may sometimes be ignored.

To cope with the problem, an improvement in accuracy of the determination on whether an abnormality has occurred while a vehicle is running, which is made by an abnormality detecting device that monitors the health condition of an occupant by detecting the biological information of the occupant, will be described in the following description.

Figure 20:
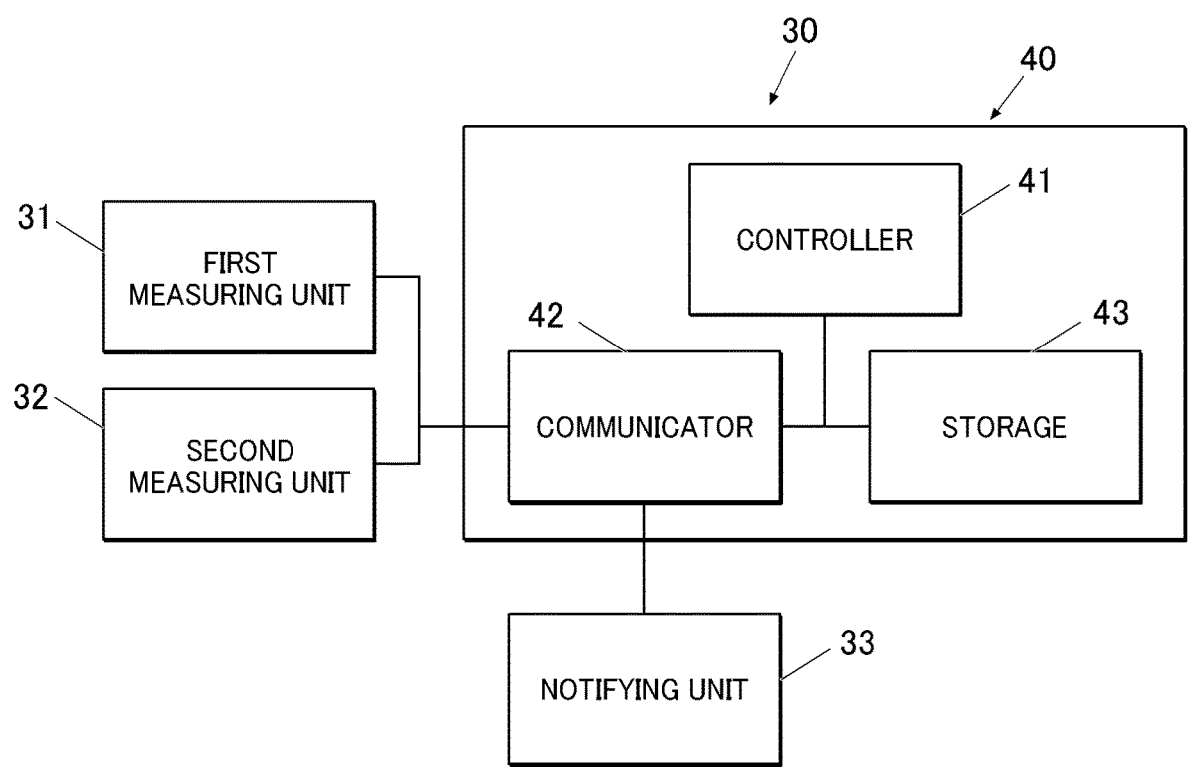
FIG. 20 is a block diagram of an abnormality detecting device according to an embodiment of the present invention, illustrating the configuration thereof.
Figure 22:
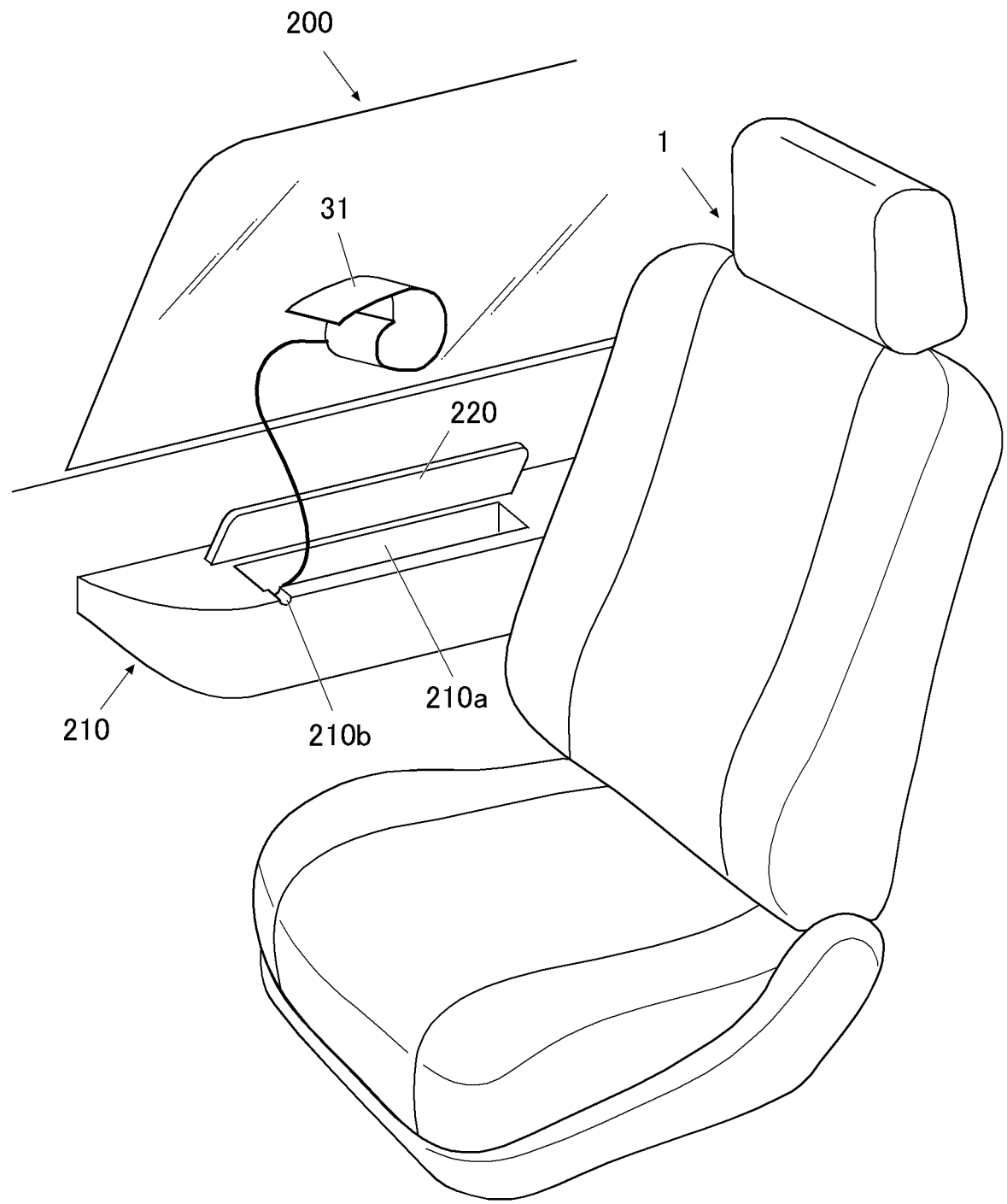
FIG. 22 is a perspective view of a seat and a vehicle door with the abnormality detecting device in FIG. 20.
Figure 23:
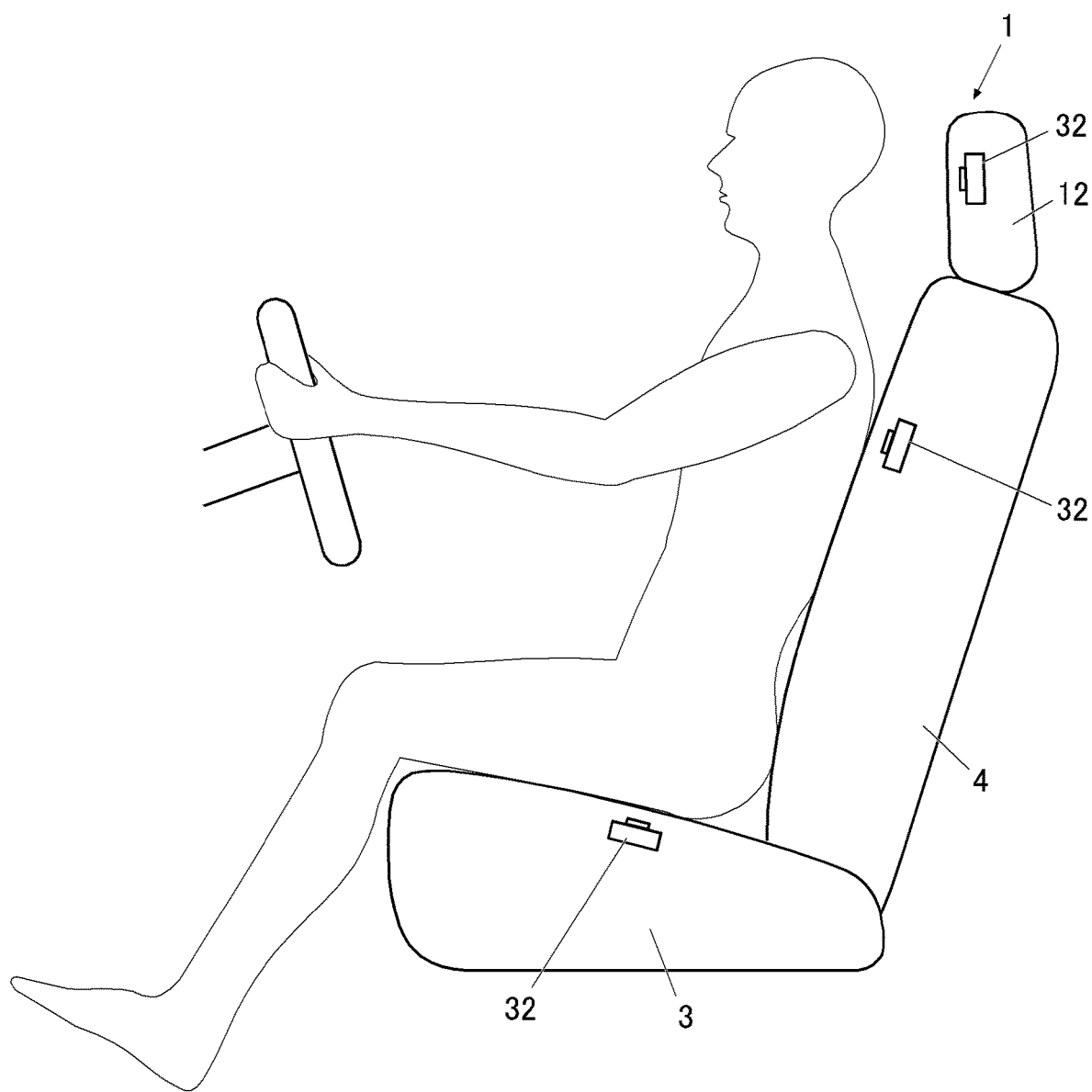
FIG. 23 is a side view of the seat with the abnormality detecting device in FIG. 20.

First, the schematic configuration of the abnormality detecting device according to an embodiment of the present invention will be described. FIG. 20 is a block diagram of the abnormality detecting device, FIG. 21 is a perspective view of a seat 1 with the abnormality detecting device 30, FIG. 22 is a perspective view of a vehicle door 200 with the abnormality detecting device 30 and a seat 1, and FIG. 23 is a side view of the seat 1 with the abnormality detecting device 30.

Figure 21:
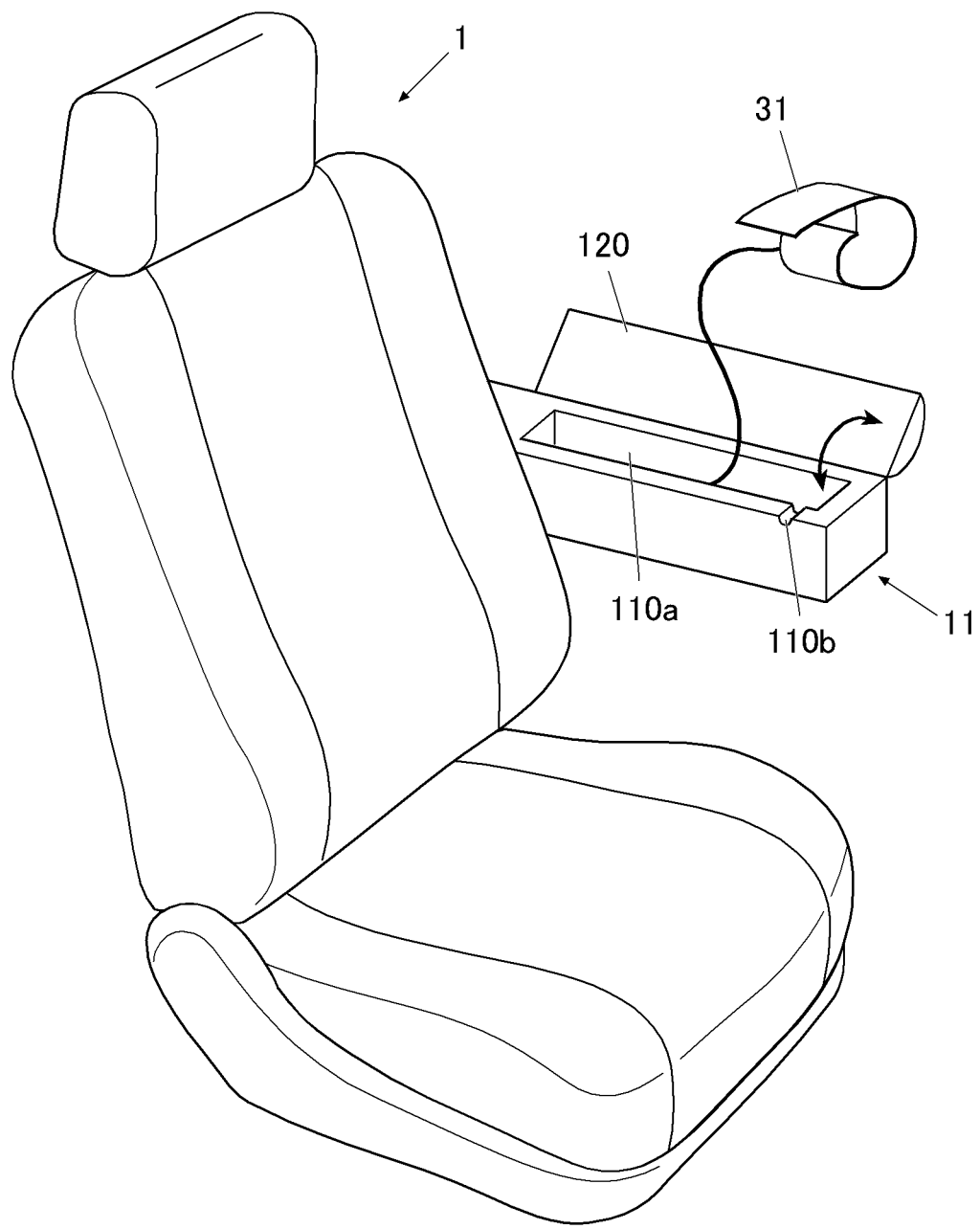
FIG. 21 is a perspective view of a seat with the abnormality detecting device in FIG. 20.

FIG. 21 illustrates an example in which the vehicle door is a passenger car door. However, the present invention is also applicable to other types of automobiles such as buses and trucks and other types of vehicles such as railways, ships and aircrafts in addition to automobiles.

The abnormality detecting device 30 according to the embodiment is installed in a vehicle in order to monitor whether there is an abnormality in the health condition of the occupant. As illustrated in FIG. 20, the abnormality detecting device 30 includes a first measuring unit 31, a second measuring unit 32, a notifying unit 33, a device main body 40 and the like.

They are connected to each other in a wired or wireless manner so that communication is possible. When connected in a wired manner, wire harnesses of the vehicle may be used. Alternatively, a dedicated wiring may be provided. When connected in a wireless manner, it is preferred to use near field wireless communication such as BLUETOOTH (registered trademark).

The first measuring unit 31 measures the biological information on the occupant including at least one of the body temperature, the pulse, the blood pressure, and the breathing rate by direct contact with the occupant. Since they are basic biological information, it is possible to understand the relatively correct health condition of the occupant by measuring any one of them.

The first measuring unit 31 may be constituted by a dedicated device or by a commercially available digital blood pressure monitor or electronic thermometer equipped with a communicating function. In terms of the configuration, the first measuring unit 31 may be installed in the vehicle. Alternatively, the first measuring unit 31 may be physically separated from the vehicle and wearable by the occupant, for example, in the form of a ring or a wristband.

The first measuring unit 31 may be configured to measure more advanced biological information such as brain waves, blood sugar level, electrocardiogram, and blood oxygen level.

Further, the first measuring unit 31 calculates the actual measured value of the detected biological information, i.e. quantifies the biological information. The actual measured value may be calculated by a controller 41 of the device main body 40, which will be described later.

Further, the first measuring unit 31 sends the calculated actual measured value to the device main body 40.

When the first measuring unit 31 and the device main body 40 are connected with each other in a wireless manner, it is preferred that the first measuring unit 31 includes a built-in battery.

It is not particularly limited where the first measuring unit 31 is disposed. For example, as illustrated in FIG. 21 and FIG. 22, the first measuring unit 31 may be disposed in an arm rest 11 of the seat or an arm rest 210 of the door 200.

In these cases, it is preferred that housings 110a, 210a are formed in the upper surfaces of the arm rests 11, 210. This allows the first measuring unit 31 (a cuff of a blood pressure monitor) to be housed when not in use, so that the first measuring unit 31 is less likely to interrupt driving of the vehicle.

Further, in these cases, it is preferred to provide covers (lids) 120, 220 for closing and opening the housings 110a, 210a. This allows closing the cover when the first measuring unit 31 is housed, so that the appearance of the vehicle is not deteriorated when the first measuring unit 31 is not in use.

Further, in these cases, it is preferred to provide grooves 110b, 210b for placing a cable from the first measuring unit 31 in the side surface of the arm rest 11 so that the covers can be closed even when the first measuring unit 31 is out of the housings. This allows measurement to be performed in a relaxed position in which the arm is placed on the closed covers 120, 220.

The second measuring unit 32 indirectly measures the same type of condition of the occupant as the condition measured by the first measuring unit 31 based on the information obtained from the occupant (reflected or transmitted light or electromagnetic waves, or the like). That is, when the first measuring unit 31 measures the blood pressure, the second measuring unit 32 measures the blood pressure.

The second measuring unit 32 may be configured as a dedicated device. Alternatively, a commercially available biosensor or any of the above-described biosensors 19, 20 to 23 or the like may be used as the second measuring unit 32.

In response to receiving a control signal from the device main body 40, the second measuring unit 32 outputs light, a pressure wave (sound wave or electromagnetic wave), vibration or the like toward the occupant. As used herein, an electromagnetic wave means an electromagnetic wave in a broad sense, including a radio wave of approximately 100 MHz and a microwave as well as infrared light, visible light, ultraviolet light, X ray, and the like. A suitable electromagnetic wave is used within the range in which the human body is not harmed.

The second measuring unit 32 detects light that has been reflected on the body surface of the occupant or that has passed through the occupant, pressure waves or the like. This eliminates the necessity of contacting the second measuring unit 32 with the occupant, and it is possible to provide the second measuring unit 32 in a relatively arbitral position.

The second measuring unit 32 calculates an estimated value of the biological information from the intensity of the detected light, electromagnetic waves or the like, i.e. quantifies the intensity. The estimated value may be calculated by a controller 41 of the device main body 40, which will be described later.

Further, the second measuring unit 32 receives a control signal to start a measurement from the device main body 40 and sends the calculated estimated value to the device main body 40.

The power source for the second measuring unit 32 and the manner of connection between the second measuring unit 32 and the device main body 40 are not particularly limited. However, since the second measuring unit 32 is required to continuously detect the biological information while the vehicle is running, it is preferred to connect the second measuring unit 32 with the device main body 40 in a wired manner so that electric power is supplied from the device main body 40.

It is possible to provide one or more second measuring units 32 to the single seat 1.

The attaching position of the second measuring unit 32 is not particularly limited. However, to allow light or electromagnetic waves emitted from the second measuring unit 32 to be transmitted without attenuation, preferred are the parts of the seat 1 that are close to the seated occupant, specifically the upper surface part of the seat cushion 3, the front surface part of the seat back 4, and the front surface part of the head rest 12 as illustrated in FIG. 23.

When the seat 1 includes an ottoman, a foot rest, a neck rest or the like (not illustrated in the figures), the second measuring unit 32 may also be disposed in such members.

For example, the notifying unit 33 is constituted by a monitor, a speaker, a vibrator or the like. According to a control signal received from the device main body 40, which will be described later, the notifying unit 33 notifies the occupant of whether there is an abnormality by means of displaying, sound, vibration or the like.

When the notifying unit 33 is constituted by a vibrator, it is preferred to provide the notifying unit 33 at a part of the seat 1 that is close to the occupant in the seat.

When the notifying unit 33 is constituted by a monitor, it is preferred to provide the notifying unit 33 in a position visually recognizable by the subject to be measured. Specifically, it is preferred to provide the notifying unit 33 in front of the seat 1 (in the case of an automobile, at an instrumental panel or, if the automobile has front and rear seats, the back surface of a front seat).

When the notifying unit 33 is constituted by a monitor, it is possible to constantly display an actual measured value and an estimated value as well as a notification of the occurrence of an abnormality. In this case, the controller 41 and the notifying unit 33 function as a notifying means of the present invention. This allows checking the current biological information even when there is no abnormality.

As illustrated in FIG. 20, the device main body 40 includes the controller 41, a communicator 42 and a storage 43.

The controller 41 is configured to integrally control the components of the device main body 40 by a CPU and a RAM. Specifically, in response to the engine of the vehicle being started, the occupant sitting down in the seat, receiving a signal from the first measuring unit 31 or the second measuring unit 32, or the like, the controller 41 reads out a variety of processing programs stored in the storage 43, develops them in the RAM and executes a variety of processing according to the processing programs.

The communicator 42 is capable of receiving an actual measured value and an estimated value from the first measuring unit 31 and the second measuring unit 32, sending a control signal to the notifying unit 33, and sending and receiving a control signal to and from a controlling device of the vehicle (not illustrated in the figures).

The storage 43 is constituted by an HDD (Hard Disk Drive), a semiconductor memory, and the like. In the storage 43, the variety of processing programs, and a predetermined numerical range and thresholds to be used for execution of the programs are stored.

The stored numerical range is in regard to the item to be measured by the first measuring unit 31 and the second measuring unit 32, which indicates a standard range (i.e. normal level) of the item to be measured. A plurality of numerical ranges may be stored corresponding to a plurality of items to be measured, and a numerical range may be selectable therefrom according to the first measuring unit 31 and the second measuring unit 32 to be connected.

The thresholds include an upper threshold that is greater than the upper end of the corresponding numerical range by a predetermined value, and a lower threshold that is less than the lower end of the numerical range by a predetermined value. Depending on the item to be measured, only either one of the upper and lower thresholds may be stored.

The storage 43 is capable of storing an actual measured value received from the first measuring unit 31 and an estimated value received from the second measuring unit 32.

The controller 41 of the device main body 40, having the above-described configuration, operates as follows according to the processing programs stored in the storage 43.

For example, the controller 41 repeatedly sends instruction signals to start the biological information to the second measuring unit 32 through the communicator 42 at predetermined regular intervals.

Figure 24:
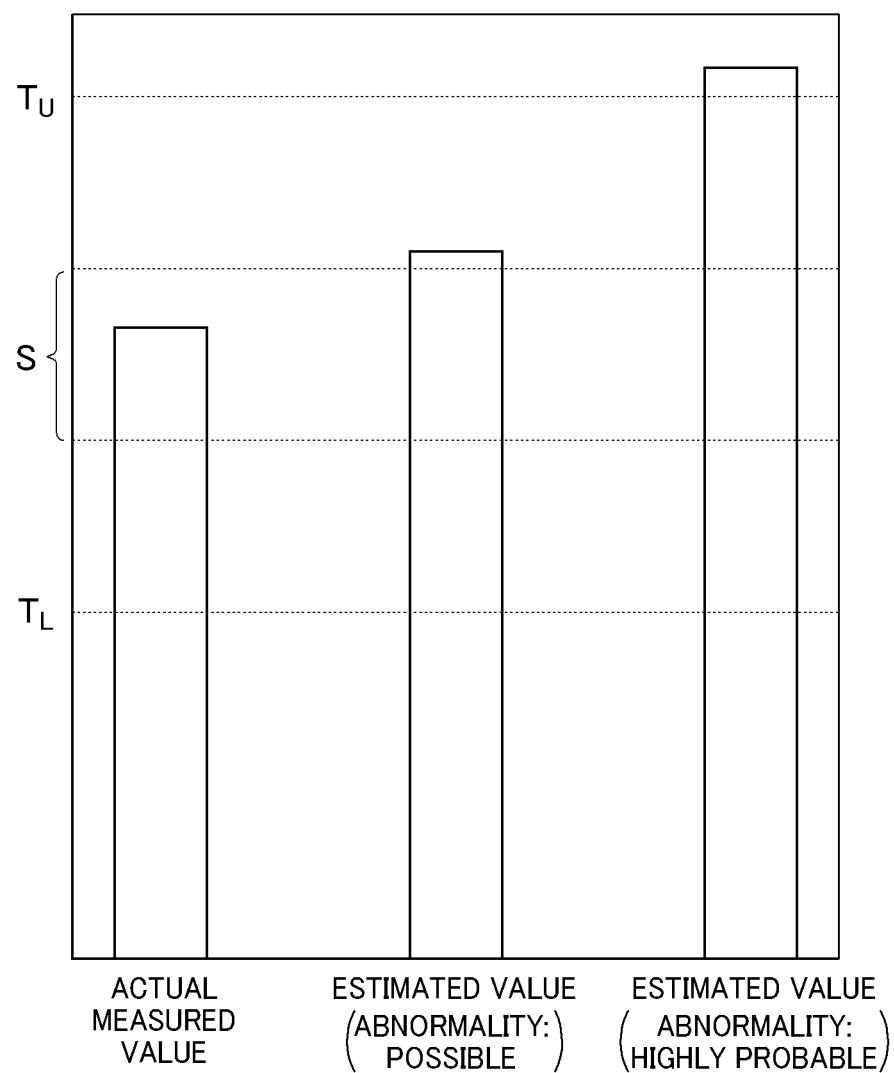
FIG. 24 is a conceptual view illustrating determination of whether there is an abnormality, which is made by the abnormality detecting device in FIG. 20.

Further, every time the controller 41 receives an estimated value from the second measuring unit 32, the controller 41 compares it with the predetermined numerical range S stored in the storage (see FIG. 24). If the estimated value is within the numerical range S, the controller 41 determines that there is no abnormality. If the estimated value is out of the numerical range, the controller 41 determines that there is an abnormality. That is, the second measuring unit 32 and the controller 41 function as a determining means of the present invention. In this configuration, it is possible to correct the determination criteria by using a relatively simple program (mechanism).

When the occupant is relatively free to operate the first measuring unit 31 (e.g. while the vehicle is stopped or in autonomous driving), the controller 41 may determine the health condition of the occupant based on an actual measured value. Since the measurement by the first measuring unit 31 is mainly made while the vehicle is stopped, this configuration allows determination of whether there is an abnormality to be made before the occupant starts (resumes) to drive the vehicle. As a result, it is possible to prevent the occupant with an abnormality from driving the vehicle.

If the controller 41 determines that the estimated value is out of the numerical range S, it then compares the estimated value with the predetermined thresholds $T_U$, $T_L$ stored in the storage (see FIG. 24). If the estimated value is between the upper end of the numerical range S and the upper threshold $T_U$ or between the lower end of the numerical range S and the lower threshold $T_L$, the controller 41 determines that a first abnormality has occurred, i.e. it is probable that an abnormality has occurred. If the estimated value is greater than the upper threshold $T_U$ or less than the lower threshold $T_L$, the controller 41 determines that a second abnormality, which is a higher level of abnormality than the first abnormality, has occurred, i.e. it is highly probable that an abnormality has occurred.

If it is determined that the estimated value is out of the numerical range S, the controller 41 sends a signal for notification of the determination result to the notifying unit 33.

Specifically, if it is determined that the first abnormality has occurred, the controller 41 sends a control signal of instruction to issue a comparatively weak first warning. If it is determined that the second abnormality has occurred, the controller 41 sends a control signal of instruction to issue a second warning that is stronger than the first warning.

In this way, when the first abnormality occurs, the notifying unit 33 issues the first warning (e.g. a notification that there is an abnormality). Further, when the second abnormality occurs, the notifying unit 33 issues the second warning (e.g. a suggestion to stop driving the vehicle). Thus, the occupant is alerted. That is, the notifying unit 33 and the controller 41 function as a warning means of the present invention. With this function, the occupant and a fellow passenger who have received the warning can prepare for an event of the occupant suddenly becoming ill. Further, based on the type of warning issued, they can understand the level of the abnormality of the occupant. This enables more correctly responding to the condition of the occupant.

The notifying unit 33 may be capable of displaying a certain screen or outputting a certain voice even when there is no abnormality.

The communicator 42 may be capable of communicating with a mobile terminal (not illustrated in the figures). If the controller 41 determines that the estimated value has changed beyond the thresholds $T_U$, $T_L$ in the direction away from the numerical range S (the warning means issues the second warning), the communicator 42 may send to the mobile terminal a control signal of instruction to contact an emergency contact person. This enables promptly calling a help when an abnormality occurs. Further, even if it becomes difficult for the occupant to operate the mobile terminal due to a muzziness or the like, he/she can call a help as long as he/she can speak. This increases the probability of being successfully rescued.

The communicator 42 may be capable of communicating with the controller of the vehicle in which the seat is installed. If the controller 41 determines that the estimated value has changed beyond the thresholds $T_U$, $T_L$ in the direction away from the numerical range S (the warning means issues the second warning), the communicator 42 may send to the controller of the vehicle a signal of instruction to restrict further driving of the vehicle (e.g. a signal to prohibit starting the engine if the vehicle is stopped, or a signal to slow down or stop the vehicle if the vehicle is running). With this configuration, it is possible to prevent the occurrence of a severe accident, for example, even if the occupant unintentionally presses down the accelerator when an abnormality occurs.

In response to receiving an actual measured value from the first measuring unit 31, the controller 41 is capable of correcting the numerical range S based on the actual measured value.

Figure 25:
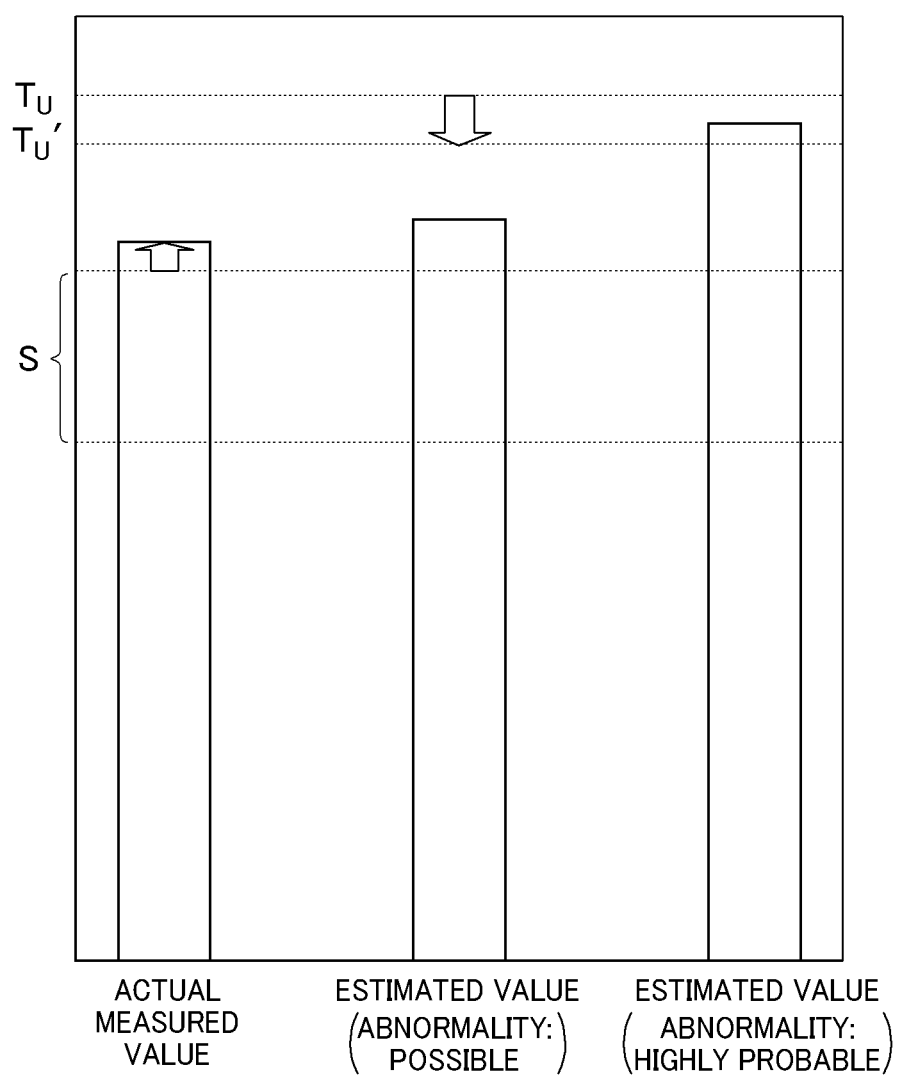
FIG. 25 is a conceptual view illustrating correction of the determination criteria by the abnormality detecting device in FIG. 20.

Specifically, if it is determined that the actual measured value is out of the numerical range S, the controller 41 narrows the numerical range S or shifts the thresholds $T_U$, $T_L$ toward the numerical range S as illustrated in FIG. 25 so that an estimated value that is subsequently obtained is more likely to be out of the numerical range S, i.e. the controller 41 is more likely to determine that an abnormality has occurred. Specifically, the controller 41 makes a correction of decreasing the upper end of the numerical range and/or the upper threshold $T_U$ when the actual measured value is greater than the upper end of the numerical range, or a correction of increasing the lower end of the numerical range S and/or the lower threshold IL when the actual measured value is less than the lower end of the numerical range. With this configuration, it is possible to find an abnormality of the occupant earlier.

The controller 41 may have a function of storing an actual measured value and a function of performing a variety of calculations on the actual measured value. When no measurement by the first measuring unit 31 is made while the occupant is in the seat, the controller 41 may correct the determination criteria based on an actual measured value in the past, the average or the median of a plurality of actual measured values in the past, the tendency of change of the plurality of actual measured values in the past, or the like. With this configuration, it is possible to correct the numerical range S and the thresholds $T_U$, $T_L$ to be closer to the reality even when the latest actual measured value cannot be obtained.

Next, a flow of driving the vehicle equipped with the above-described abnormality detecting device 30 will be described based on an example in which the vehicle is an automobile.

First, the occupant sits down in the seat of the vehicle and starts the engine. In this step, the abnormality detecting device 30 is activated so that the first measuring unit is ready for making a measurement.

Then, the occupant takes the first measuring unit 31 (e.g. a cuff of a blood pressure monitor) out of the seat (e.g. the housing 110a, 210a of the arm rest 11, 210) and brings it into contact with his/her own body surface (e.g. wraps it around the arm) to measure the biological information (blood pressure). If there is an abnormality in the occupant (the actual measured value is out of the numerical range S), the controller 41 of the device main body 40 corrects the numerical range S to narrow it.

When the occupant starts driving the vehicle (a predetermined period of time has passed) without making a measurement, the controller 41 retrieves a past actual measured value. When there is a problem in the past actual measured value, the controller 41 corrects the numerical range S. When there is a problem in the past actual measured value, the controller 41 corrects the numerical range S.

After the occupant starts driving the vehicle, the second measuring units 32 repeatedly determines an estimated value of the biological information by periodically emitting light or electromagnetic waves to the occupant. While the estimated value is within the numerical range S, the notifying unit 33 does not issue any warning and the occupant can continue to drive the vehicle uneventfully.

However, when the estimated value is changed to be out of the numerical range S, the notifying unit 33 issues the first warning or the second warning depending on the extent of deviation.

In this way, the vehicle equipped with the abnormality detecting device 30 of the embodiment keeps monitoring whether there is an abnormality in the occupant while he/she is driving the vehicle. Therefore, it is possible to find the occurrence of an abnormality of the occupant immediately.

Figure 26:
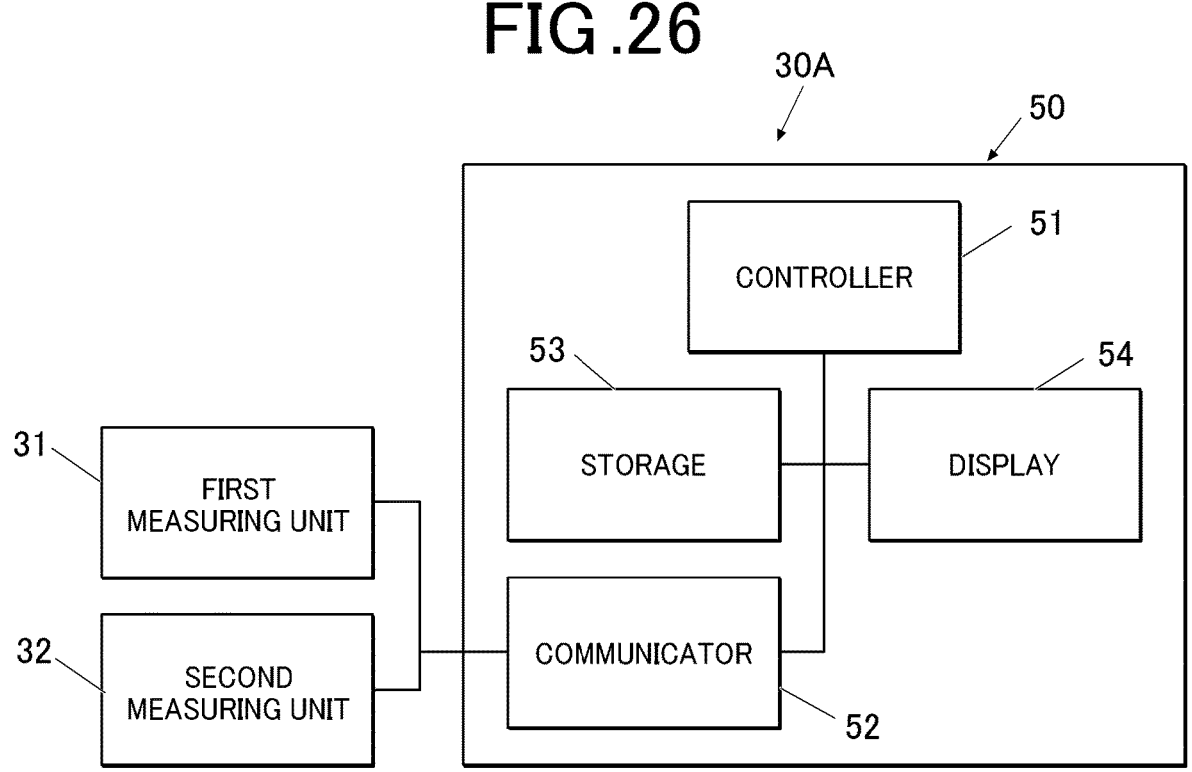
FIG. 26 is a block diagram of the abnormality detecting device according to a variation of the embodiment, illustrating the configuration thereof.

In one or more embodiments of the present invention, a mobile terminal 50 such as a commercially available smartphone or tablet may be provided as illustrated in FIG. 26 in place of the notifying unit 33 and the device main body 40.

With a predetermined application preinstalled in a storage 53, a controller 51 and a communicator 52 of the mobile terminal 50 fulfill the same functions as the controller 41 and the communicator 42 of the device main body 40 of the above-described embodiment.

Further, a display 54, and a speaker and a vibrator (not illustrated in the figure) of the mobile terminal 50 fulfill the same functions as the notifying unit 33 of the embodiment.

An abnormality detecting device 30A having this configuration eliminates the necessity to produce the dedicated device main body and the notifying unit. Therefore, it is possible to reduce the production cost of the abnormality detecting device. Further, it is possible to give a notification by various means such as displaying an image, voice and vibration. It is also possible to utilize a mobile terminal owned by the occupant.

Regarding techniques of understanding the health condition of a driver that involve detecting and estimating the biological information such as the blood flow and the blood pressure based on measurement results such as pulse wave by non-contact blood flow sensors embedded in the sitting surface and the backseat surface of a seat, techniques described in JP 2016-190022A and JP 2016-077890A are also known in the art.

However, as described in these documents, particularly in JP 2016-077890A, it requires complicated processing to determine a blood pressure based on information individually obtained from a camera and a sensor, which results in the higher production cost of the device.

Further, such complicated processing causes a delay in determination of whether the blood pressure is normal or not. For example, an occupant who is driving a vehicle may fall into a critical condition before the device determines that there is an abnormality in the health condition of the occupant. In such cases, the occupant may lose control of the vehicle and have an accident.

To cope with such problems, hereinafter, measures for reducing the production cost and achieving rapid determination in an abnormality detecting device that monitors the health condition of an occupant by using a plurality of detecting means for detecting the biological information of the occupant will be described.

In the following, two configuration examples will be described.

Configuration Example 1

Figure 27:
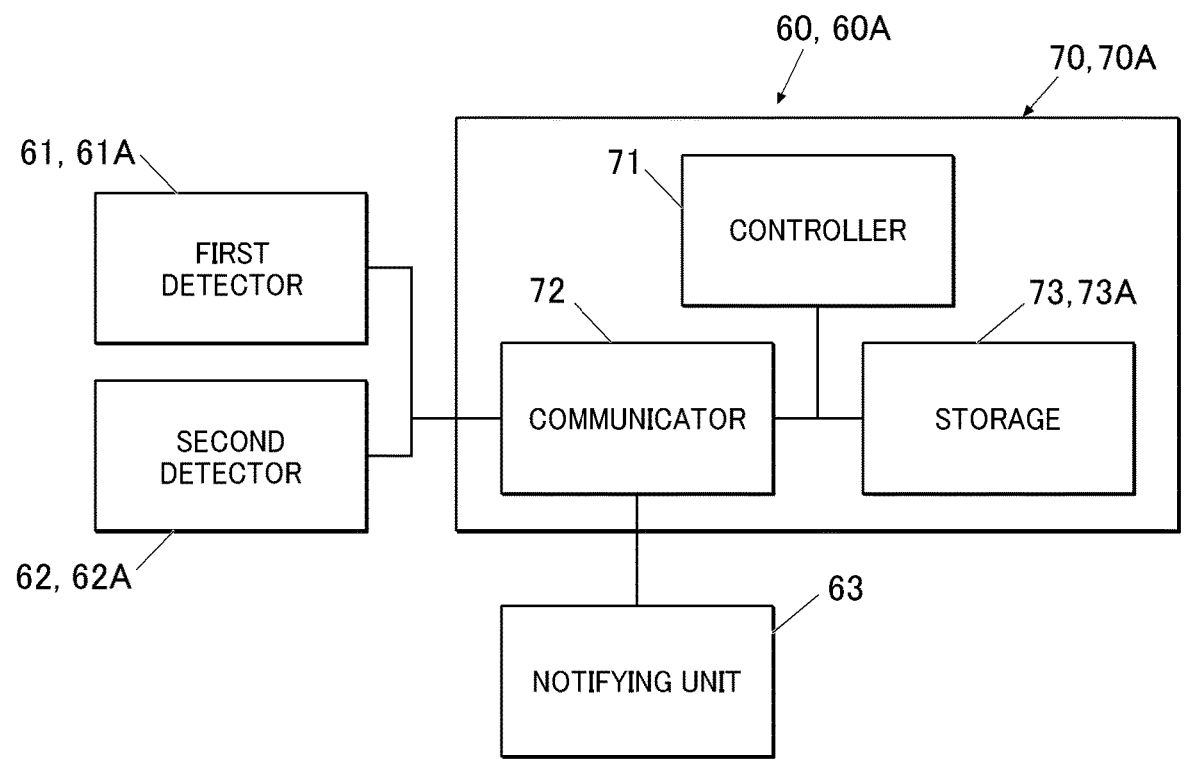
FIG. 27 is a block diagram of an abnormality detecting device according to Configuration Example 1 and Configuration Example 2.

First, the schematic configuration of an abnormality detecting device according to Configuration Example 1 of the present invention will be described. FIG. 27 is a block diagram of the abnormality detecting device 60, FIG. 28 is a schematic view from the rear side of an occupant room of a vehicle 100 with the abnormality detecting device 60, and FIG. 29 is a side view of a seat 1 with the abnormality detecting device 60.

Figure 28:
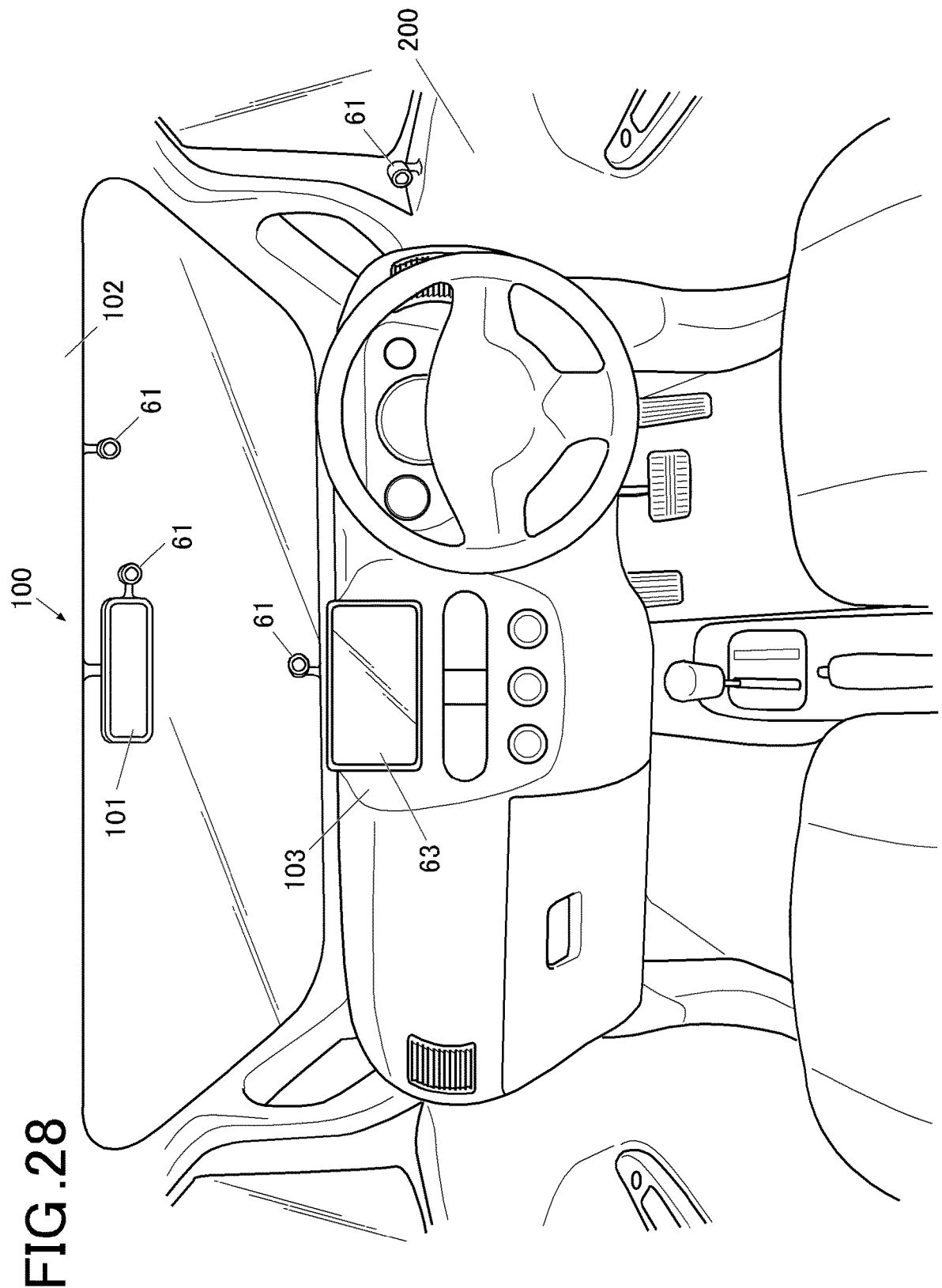
FIG. 28 is a schematic rear view of an occupant room of a vehicle with the abnormality detecting device in FIG. 27.
Figure 29:
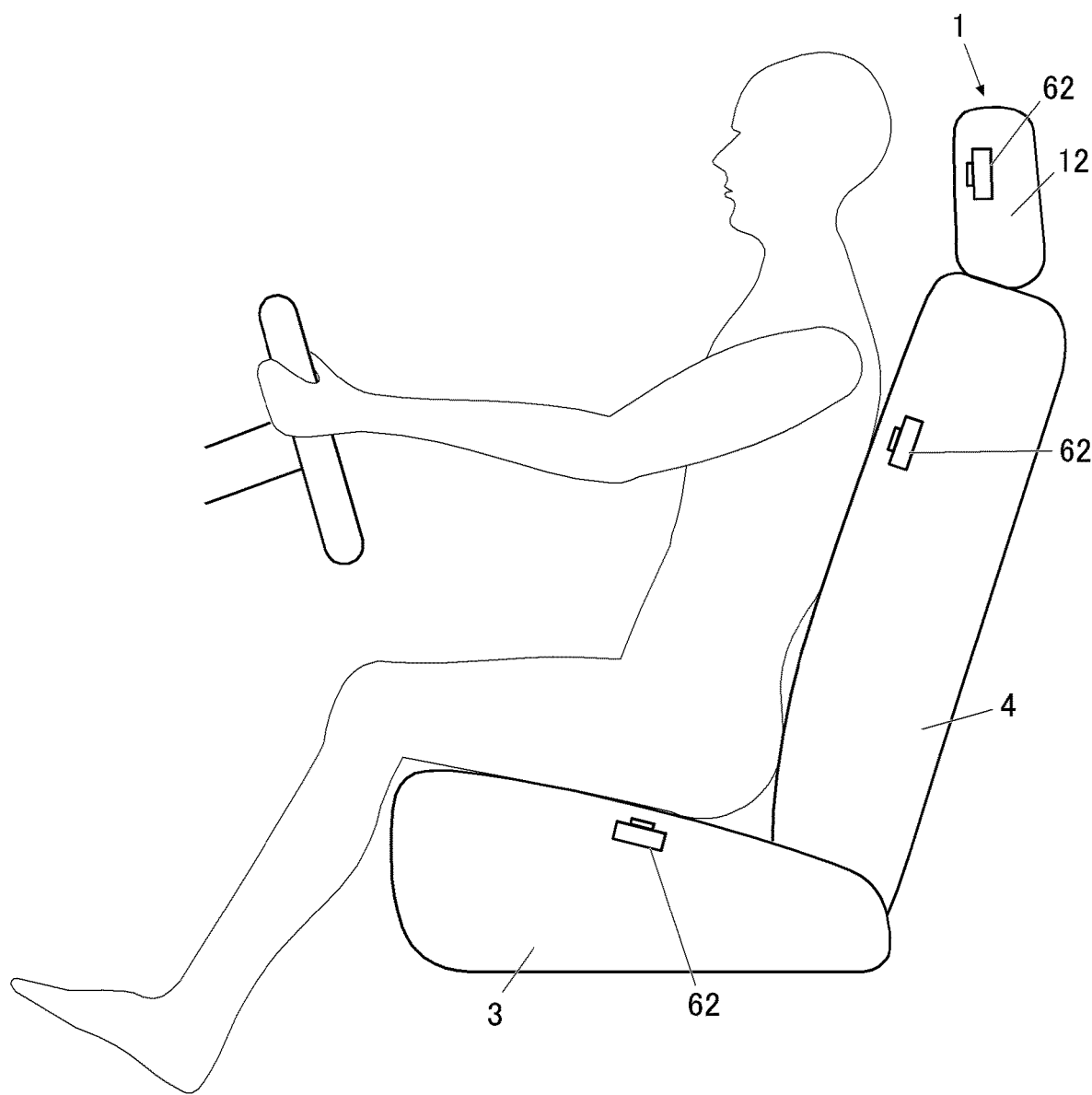
FIG. 29 is a side view of a seat with the abnormality detecting device in FIG. 27.

FIG. 28 illustrates an example in which the occupant room of the vehicle 100 is that of a passenger car. However, the present invention is also applicable to other types of automobiles such as buses and trucks and other types of vehicles such as railways, ships and aircrafts in addition to automobiles.

The abnormality detecting device 60 according to Configuration Example 1 is installed in the vehicle 100 in order to monitor whether an abnormality occurs in the health condition of the occupant. As illustrated in FIG. 27, the abnormality detecting device 60 includes a first detector 61, a second detector 62, a notifying unit 63, and a device main body 70.

These components are connected with each other in a wireless or wired manner. When connected in a wired manner, wire harnesses of the vehicle may be used. Alternatively, a dedicated wiring may be provided. When connected in a wireless manner, it is preferred to use near field wireless communication such as BLUETOOTH (registered trademark).

The first detector 61 is provided to detect the condition of the occupant including his/her biological information. In this configuration example, the first detector 61 is constituted by a camera. The camera may be a still camera for capturing a still image or a video camera for capturing a video (motion picture). However, preferred is a video camera since it is required to keep capturing an image/video showing the condition of the occupant while the occupant is in the vehicle.

The first detector 61 may be constituted by a dedicated device or a commercially available camera with a communicating function.

The manner of connection between the first detector 61 and the device main body 70 is not particularly limited. However, since the first detector 61 is expected to be used for a long period of time, it is preferred to connect the first detector 61 with the device main body in a wired manner so that electric power is supplied from the device main body 70.

In response to receiving a control signal from the device main body 70, the first detector 61 starts capturing an image/video or stops the capture.

Further, the first detector 61 sends image data on the captured image to the device main body 70.

It is possible to provide one or more first detectors 61 to a single vehicle.

Although it depends on the type of the vehicle, the position of the first detector 61 is not particularly limited, and the first detector 61 may be disposed in any position from which an image/video of the occupant can be captured.

When the vehicle is an automobile, the first detector 61 may be provided at a back mirror 101, a ceiling 102, an instrument panel 103, a door 200 or the like as illustrated in FIG. 28 so as to be able to capture an image/video from a rear angle.

FIG. 28 illustrates an example in which the first detector 61 is provided only around a driver seat. However, the first detector 61 may be provided around other seats such as a front passenger seat.

When the vehicle to which the present invention is applied has multi-line seats arrayed in the front-rear direction, the first detector 61 may be provided at the back surface of a front seat so as to be able to capture an image/video from an angle toward a rear seat.

The second detector 62 detects the conditions of the occupant by a method different from that of the first detector 61. In this configuration example, the second detector 62 detects the biological information of the occupant including at least one of the body temperature, the pulse, the blood pressure and the breathing rate directly by a contact with the occupant or indirectly based on information (e.g. reflected or transmitted light or electromagnetic waves) obtained from the occupant.

The second detector 62 may be configured as a dedicated device. Alternatively, the second detector 62 may be constituted by a commercially available blood pressure monitor, thermometer or biosensor or any of the above-described biosensors 19, 20 to 23 or the like equipped with a communicating function.

When the second detector 62 indirectly detects the conditions, the second detector 62 is configured to output light, pressure waves (sound waves or electromagnetic waves), vibration or the like toward the occupant in response to receiving a control signal from the device main body 70. As used herein, an electromagnetic wave means an electromagnetic wave in a broad sense, including a radio wave of approximately 100 MHz and a microwave as well as infrared light, visible light, ultraviolet light, X ray, and the like. A suitable electromagnetic wave is used within the range in which the human body is not harmed.

In this case, the second detector 62 is configured to detect light, pressure waves or the like that has been reflected on the body surface of the occupant or that has passed through the occupant. This eliminates the necessity of contact with the occupant, and it is possible to provide the second detector 62 in a relatively arbitral position.

The second detector 62 calculates a second detected value based on the detected information. A first detected value will be described later. The second detected value may be calculated by a controller 71 (described later) of the device main body 70.

Further, the second detector 62 receives a control signal of instruction to start a measurement from the device main body 70 and sends the calculated second detected value to the device main body 70.

The manner of connection between the second detector 62 and the device main body 70 is not particularly limited. However, since the second detector 62 is required to continuously detect the conditions of the occupant while the vehicle is running, it is preferred to connect the second detector 62 with the device main body 70 in a wired manner so that electric power is supplied from the device main body 70.

It is possible to provide one or more second detectors 62 to the single seat 1.

The attaching position of the second detector 62 is not particularly limited. However, to allow light or electromagnetic waves emitted from the second detector 62 to be transmitted without attenuation, preferred are the parts of the seat 1 that are close to the seated occupant, specifically the upper surface part of the seat cushion 3, the front surface part of the seat back 4, and the front surface part of the head rest 12 as illustrated in FIG. 29.

When the seat 1 includes an ottoman, a foot rest, a neck rest or the like (not illustrated in the figure), the second detector 62 may be disposed in such members.

For example, the notifying unit 63 is constituted by a monitor, a speaker, a vibrator or the like. According to a control signal received from the device main body 70, which will be described later, the notifying unit 63 notifies the occupant of whether there is an abnormality by means of displaying, sound, vibration or the like.

When the notifying unit 63 is constituted by a vibrator, it is preferred to provide the notifying unit 63 at a part of the seat 1 that is close to the occupant in the seat.

When the notifying unit 63 is constituted by a monitor, it is preferred to provide the notifying unit 63 in a position visually recognizable by the subject to be measured. Specifically, it is preferred to provide the notifying unit 63 in front of the seat 1 (in the case of an automobile, at an instrumental panel 103 or, if the automobile has multi-line seats in the front-rear direction, the back surface of a front seat).

When the notifying unit 63 is constituted by a monitor, it is possible to display a captured image or a detected value by the first detector 61 according to need as well as a notification of the occurrence of an abnormality. This allows checking the current biological information of the occupant even when there is no abnormality.

As illustrated in FIG. 27, the device main body 70 includes the controller 71, a communicator 72, a storage 73 and the like.

The controller 71 is configured to integrally control the components of the device main body 70 by a CPU and a RAM. Specifically, in response to the engine of the vehicle being started, the occupant sitting down in the seat, receiving a signal from the first detector 61 or the second detector 62, or the like, the controller 71 reads out a variety of processing programs stored in the storage 73, develops them in the RAM and executes a variety of processing according to the processing programs.

The communicator 72 is capable of sending a control signal to the first detector 61 and the second detector 62, receiving image data from the first detector 61, receiving a second detected value from the second detector 62, sending a control signal to the notifying unit 63, and sending and receiving a control signal to and from a controlling device (not illustrated in the figures) of the vehicle 100.

The storage 73 is constituted by an HDD (Hard Disk Drive), a semiconductor memory and the like. In the storage 73, the variety of processing programs, and a predetermined threshold and a numerical range for execution of the programs are stored.

Examples of the threshold include the area ratio of a pupil in an area recognized as an eye (the number of pixels with low density) or the distance between the upper eyelid and the lower eyelid when the eye is open, and the upper end of the normal range of the moving distance or the moving speed of a part recognized as the head.

The numerical range is in regard to the item to be measured by the second detector 62 or the item to be measured by the first detector 61 that detects the biological information, which indicates a standard range (i.e. normal level) of the item to be measured. A plurality of numerical ranges may be stored corresponding to a plurality of items to be measured, and a numerical range may be selectable therefrom according to the second detector 62 to be connected.

The storage 73 is capable of storing detected values received from the first detector 61 and the second detector 62.

The controller 71 of the device main body 70, which is configured as described above, operates as follows according to the processing program stored in the storage 73.

For example, in response to an occupant operation, the engine of the vehicle being started, the occupant sitting down in the seat, or the like, the controller 71 sends a signal of instruction to start capturing an image/video to the first detector 61 via the communicator 72.

Further, simultaneously with or after sending the signal of instruction to start capturing an image/video, the controller 71 repeatedly sends a signal of instruction to start a measurement to the second detector 62 via the communicator 72 at predetermined regular intervals.

The controller 71 determines a first detected value from the detected condition of the occupant. Specifically, from the image data received from the first detector 61, the controller 71 directly extracts the biological information such as the pulse wave. Alternatively, the controller 71 recognizes the eyes and the head in the image and calculates, for example, the area ratio of the pupils in the eyes (ratio of black pixels), the temporal change of the distance between the upper eyelid and the lower eyelid, or the moving speed of the head. That is, the controller 71 serves as a first detecting means of the present invention.

The first detected value may be calculated by the first detector 61.

The controller 71 determines whether there is an abnormality based on the captured image. Specifically, the controller 71 makes the determination by comparing the determined first detected value with a corresponding threshold or numerical range.

In the configuration in which the pupil area or the distance between the upper and lower eyelids is used for the determination, the controller 71 determines that the eyelids are closed, i.e. the occupant may be nodding off or in a bad condition, if the first detected value remains less than the threshold for a predetermined period of time.

In the configuration in which the head movement or the like is used for the determination, the controller 71 determines that the occupant has bent the neck abnormally rapidly, i.e. the occupant may be nodding off or in a decreased level of consciousness if the first detected value is greater than the threshold.

In the configuration in which the biological information is detected from image data, the controller 71 determines the blood pressure, the breathing rate or the like as the first detected value and makes a determination as to whether there is an abnormality based on whether the first detected value is within the numerical range.

The controller 71 that performs the above-described processing serves as a determining means (first determining means) of the present invention.

Figure 30:
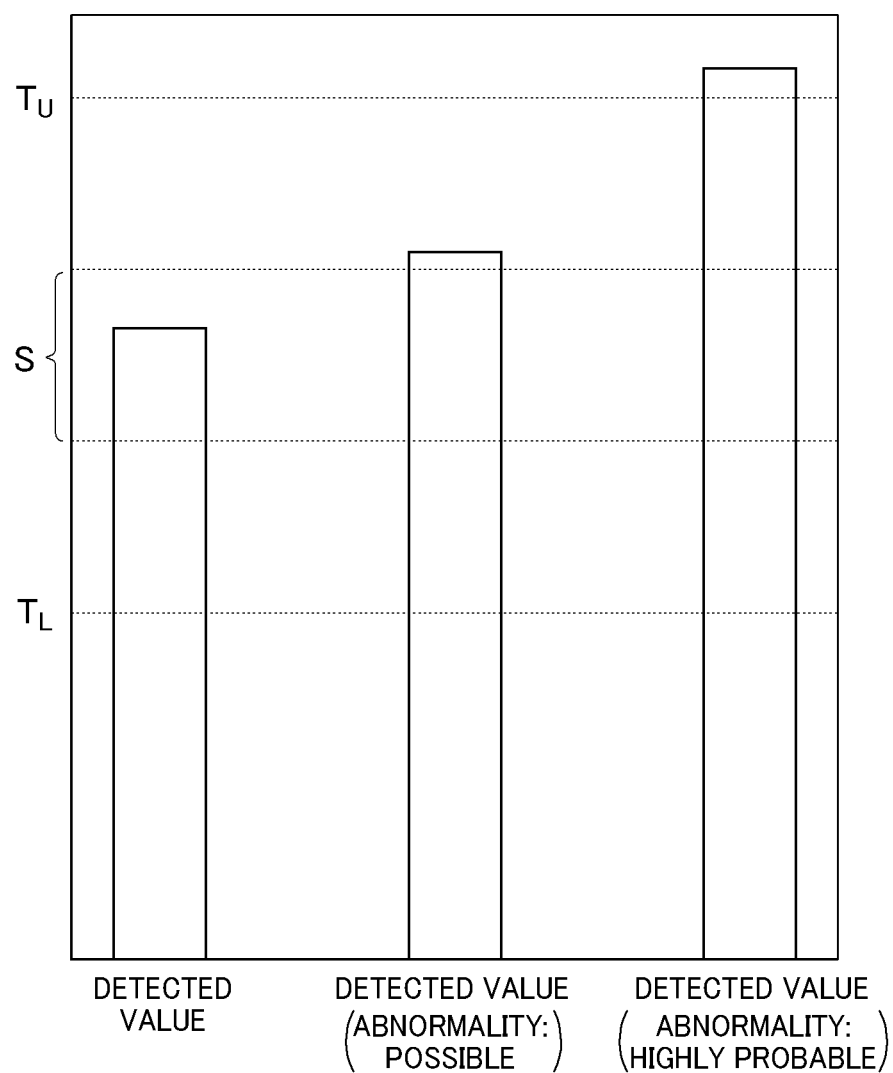
FIG. 30 is a conceptual view illustrating determination of whether there is an abnormality, which is made by the abnormality detecting device in FIG. 27.

Every time the controller 71 receives a second detected value from the second detector 62, the controller 71 compares the received value with a predetermined numerical range S stored in the storage 73 (see FIG. 30). If the second detected value is within the numerical range S, the controller 71 determines that there is no abnormality. If the second detected value is out of the numerical range S, the controller 71 determines that there is an abnormality of some kind. That is, the second detector 62 and the controller 71 function as a determining means (second determining means) of the present invention. In this configuration, it is possible to correct the determination criteria by using a relatively simple program (mechanism).

The controller 71 makes a final determination as to whether there is an abnormality by using at least one of the determination based on the first detected value and the determination based on the second detected value. That is, in this configuration example, both or one of the determination based on the first detected value and the determination based on the second detected value is used to make the final determination.

In this configuration example, both determinations are basically used to make the final determination. However, the basis of the final determination may be selectable beforehand between both determinations and one of the determinations according to a user operation or the items to be detected by the first detector 61 and the second detector 62.

The configuration in which one of the determinations is used to make the final determination will be described later.

If both the determination based on the first detected value and the determination based on the second detected value indicate that there is no abnormality, the controller 71 determines that there is no abnormality. If both determinations indicate that there is an abnormality, the controller 71 determines that there is an abnormality.

In this regard, the determination based on the first detected value may sometimes be different from the determination based on the second detected value. To cope with such situations, the device main body 70 is configured such that the setting is selectable between: (a) if one determination indicates there is no abnormality while the other indicates there is, the final determination is that there is an abnormality; (b) if one determination indicates there is an abnormality while the other indicates not, the final determination is that there is no abnormality. In this configuration, when (a) is selected, it is more likely to be determined that there is an abnormality. As a result, the health condition of the occupant can be monitored more carefully. In contrast, when (b) is selected, it is more likely to be determined that there is no abnormality. As a result, the occupant can be prevented from feeling undue anxiety.

The setting for situations in which the determination based on the first detected value is different from the determination based on the second detected value may also be selectable from: (c) a priority is given to the determination based on the first detected value (second detected value) regardless of the determination results.

When there is only a slight difference between the first detected value and the upper or lower end of the numerical range or the threshold, which means that there is a probability of the determination based on the first detected value being incorrect, the second detected value may be used for the determination. For example, it is difficult to determine the condition of the eyes (whether or not the eyelids are open) based on an image taken by the first detector 61 in a certain condition such as when the occupant who is driving the vehicle is nodding off with his/her eyelids slightly open, when it is dark in the night, or when the sunlight is strong. In such conditions, the second detected value can be used to make a determination as to whether there is a decrease in the blood pressure or the heart rate due to sleep. This allows accurate determination as to whether the occupant is nodding off. That is, the determination based on the first detected value is complemented by the second detected value.

When the first detected value or the second detected value is far away from the numerical range or the threshold, the controller 71 selects the former determination from among the determination based on the first detected value and the determination based on the second detected value and uses it as the final determination result. Specifically, for example, an upper threshold $T_U$ that is greater than the upper end of the numerical range S by a predetermined value (see FIG. 30) and a lower threshold $T_L$ that is less than the lower end of the numerical range S by a predetermined value are set. If the former determination is that the detected value is out of the numerical range S, the controller 71 further compares the detected value with the predetermined thresholds $T_U$, $T_L$ stored in the storage. If the detected value is between the upper end of the numerical range S and the upper threshold $T_U$ or between the lower end of the numerical range S and the lower threshold $T_L$, the controller 71 determines that the first abnormality has occurred, i.e. it is probable that an abnormality has occurred, and waits for the latter determination. If the detected value is greater than the upper threshold $T_U$ or less than the lower threshold $T_L$, the controller 71 determines that the second abnormality, which is a higher level of abnormality than the first abnormality, has occurred, i.e. it is highly probable that an abnormality has occurred, and uses the former determination as the final determination result without waiting for the latter determination. With this configuration, it is possible to immediately detect the occurrence of a serious abnormality and thereby to prevent the occurrence of an incident.

When the latter determination is made, the controller 71 corrects the criterion (numerical range, thresholds) of the determination as to whether there is an abnormality, based on the result of the former determination.

The way of the correction is selectable between: (a) narrowing the numerical range or shifting the thresholds toward the previous detected value; and (b) expanding the numerical range or shifting the threshold away from the previous detected value, for example, according to a user operation or the like. In this configuration, when (a) is selected, it is more likely to be determined that there is an abnormality. As a result, it is possible to find an abnormality of the occupant earlier or to monitor the health condition of the occupant more carefully. In contrast, when (b) is selected, it is more likely to be determined that there is no abnormality. As a result, the occupant can be prevented from feeling undue anxiety.

When the controller 71 determines that there is an abnormality, the controller 71 sends a signal for notification of the abnormality to the notifying unit 63.

Accordingly, when an abnormality occurs, the notifying unit 63 issues a warning (e.g. notification of the occurrence of an abnormality) to alert the occupant. That is, the notifying unit 63 and the controller 71 function as a warning means of the present invention.

The notifying unit 63 may be capable of displaying a certain screen or outputting a certain voice even when there is no abnormality.

Alternatively, when the former determination is that there is an abnormality, the controller 71 may send a signal for issuing the first warning to the notifying unit 63. Then, when the latter determination is that there is an abnormality, too, the controller 71 may send a signal for issuing the second warning (e.g. a suggestion to stop driving the vehicle), which is a higher level of warning than the first warning, to the notifying unit 63. With this configuration, it is possible to promptly notify the occupant of the occurrence of an abnormality in the health condition of the occupant by the first warning. Further, the second warning allows issuing a warning twice. Therefore, it is possible to draw attention of the occupant who did not pay attention to the first warning.

The communicator 72 may be configured to be able to communicate with a mobile terminal (not illustrated in the figures). If the controller 71 determines that the detected value has changed beyond the thresholds $T_U$, $T_L$ in the direction away from the numerical range S (the warning means issues the second warning), the communicator 72 may send to the mobile terminal a control signal of instruction to contact an emergency contact person. This enables promptly calling a help when an abnormality occurs. Further, even if it becomes difficult for the occupant to operate the mobile terminal due to a muzziness or the like, he/she can call a help as long as he/she can speak. This increases the probability of being successfully rescued.

The communicator 72 may be capable of communicating with the controller of the vehicle in which the seat is installed. If the controller 71 determines that the detected value has changed beyond the thresholds $T_U$, $T_L$ in the direction away from the numerical range S (the warning means issues the second warning), the communicator 72 may send to the controller of the vehicle a signal of instruction to restrict further driving of the vehicle (e.g. a signal to prohibit starting the engine if the vehicle is stopped, or a signal to slow down or stop the vehicle if the vehicle is running). With this configuration, it is possible to prevent the occurrence of a severe accident, for example, even if the occupant unintentionally presses down the accelerator when an abnormality occurs.

In some embodiments of the present invention, a plurality of first detectors 61 and a plurality of second detectors 62 may be provided. The determination as to whether there is an abnormality may be made based on at least two of four or more information that are obtained by the respective detectors and measuring units. With this configuration, it is possible to make the determination as to whether there is an abnormality more correctly. Further, it is possible to make a more detailed determination by changing the combination of the information to be used.

Figure 31:
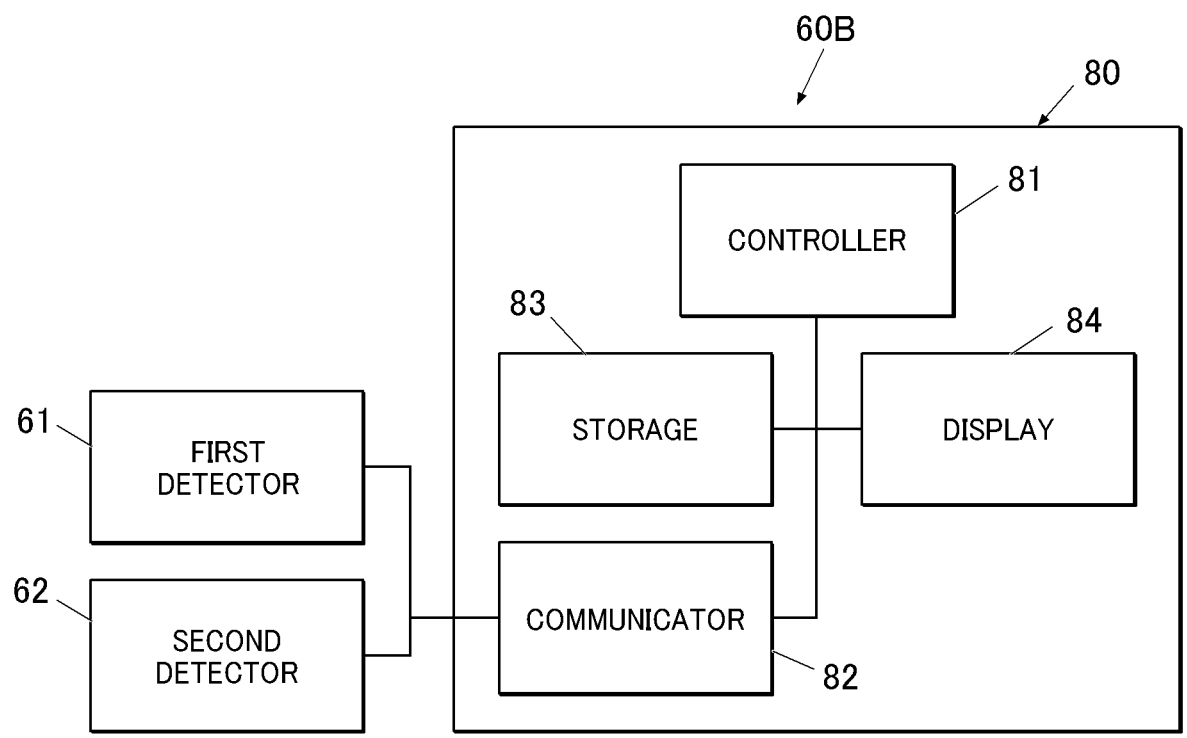
FIG. 31 is a block diagram of the abnormality detecting device according to a variation of the embodiment, illustrating the configuration thereof.

Instead of the notifying unit 63 and the device main body 70, a mobile terminal 80 such as a commercially available smartphone or a tablet may be provided as illustrated in FIG. 31.

With a predetermined application preinstalled in the storage 83, a controller 81 and a communicator 82 of the mobile terminal 80 fulfill the same functions as the controller 71 and the communicator 72 of the device main body 70 in the above-described configuration example.

Further, a display 84, a speaker (not illustrated in the figures), a vibrator and the like of the mobile terminal 80 fulfill the same functions as the notifying unit 63 in the above-described configuration example.

An abnormality detecting device 60B having this configuration eliminates the necessity to produce a dedicated device main body and notifying unit. Therefore, it is possible to reduce the production cost of the abnormality detecting device. Further, it is possible to give a notification by various means such as displaying an image, voice and vibration. It is also possible to utilize a mobile terminal owned by the occupant.

The abnormality detecting device 60 may include a means for detecting the calorie expenditure (change in condition) of the occupant in a predetermined period of time before the occupant sits down in the seat, and the controller 71 may correct the numerical range and the thresholds based on the calculated calorie expenditure. In this configuration, the means for detecting the calorie expenditure and the controller 71 function as a third detecting means of the present invention.

When the occupant has burned calories by an exercise or the like before he/she sits down in the seat, he/she is likely to have more reddish skin or higher heart rate and blood pressure than normal. It is highly probable that this leads to an erroneous determination that there is an abnormality. To avoid this, the numerical range of the biological information may be widened or the thresholds may be shifted away according to the estimated amount of increase (change in condition) due to the exercise. This can reduce the occurrence of an erroneous determination.

Configuration Example 2

Next, the schematic configuration of an abnormality detecting device according to Configuration Example 2 of the present invention will be described.

In the following, only the differences from Configuration Example 1 will be described. Omitted configurations and operations are basically the same as those of Configuration Example 1.

An abnormality detecting device 60A of Configuration Example 2 is different mainly in the configuration of a first detector 61A and a second detector 62A and the control by a device main body 70A.

The first detector 61A of this configuration example detects the biological information of the occupant including at least one of the body temperature, the pulse, the blood pressure and the breathing rate by direct contact with the occupant.

The first detector 61A may be constituted by a dedicated device or by a commercially available digital blood pressure monitor or electronic thermometer equipped with a communicating function.

The first detector 61A may be installed in the vehicle. Alternatively, the first detector 61A may be physically separated from the vehicle and wearable by the occupant, for example, in the form of a ring or a wristband.

The first detector 61A may measure more advanced biological information such as brain waves or blood sugar levels.

The first detector 61A determines a first detected value based on the detected biological information. That is, the first detector 61A serves as a first detecting means of the present invention.

The first detected value A may be calculated by the controller 71 (described later) of the device main body 70A.

The first detector 61A sends the obtained first detected value to the device main body 70A.

It is possible to provide one or more first detectors 61 to a single vehicle.

It is not particularly limited where the first detector 61A is disposed. For example, the first detector 61A may be disposed at a part that is likely to come in contact with the occupant (in particular the skin) such as an arm rest of a seat 1 or an arm rest of the door 200 (not illustrated in the figures).

The second detector 62A of this configuration example indirectly measures the same biological information as the first detector 61A based on information (reflected or transmitted light or electromagnetic waves) obtained from the occupant.

The second detector 62A may be constituted by a dedicated device or by a commercially available biosensor or any of the above-described biosensors 19, 20 to 23.

The device main body 70A is different from that of Configuration Example 1 in a processing program stored in a storage 73A.

Specifically, the device main body 70A does not have the program in Configuration Example 1 for recognizing the eyes and the head from image data and determining the first detected value based on the recognition.

Instead, a program for comparing the first detected value received from the first detector 61A with a numerical range S is stored.

In this embodiment, the abnormality detecting device can rapidly make a determination without using any camera, which can also be produced at low cost.

INDUSTRIAL APPLICABILITY

The present invention is applicable to vehicle seats and the like.

REFERENCE SIGNS LIST

V Vehicle
V1 Driving controller
P Occupant
P1 Torso
P2 Thigh
P3 Arm
P4 Head
P5 Neck
P6 Leg
P7 Foot
1 Seat
2 Seat body
3 Seat cushion
3a Cushion pad
3b Covering material
4 Seat back
4a Cushion pad
4b Covering material
5 Punched hole
6 Air path
11 Arm rest
11a Covering material
11b Opening
16 Housing
17 Covering member
18a Hook and loop fastener
18b Hook and loop fastener
12 Head rest
13 Neck rest
14 Ottoman
15 Foot rest
20 Photoelectric pulse wave sensor
20a Light emitter
20b Light receiver
21 Piezoelectric pulse wave sensor
22 Electromagnetic pulse wave sensor
23 Biosensor of different type
24 Blood pressure estimator
25 Communication/connection wire
26 Vibration-powered generating element
27 Communication/connection wire

The invention claimed is:

1. A biosensor arrangement structure, comprising:
a plurality of biosensors that is disposed in a seat for supporting an occupant and that measures a health condition of the occupant,
wherein the seat includes: a seat body for holding the occupant; and an auxiliary supporter for supporting a body part of the occupant except for a torso and thighs,
wherein at least a first sensor of the plurality of biosensors is disposed at the auxiliary supporter,
wherein at least a second sensor of the plurality of biosensors is disposed at the seat body, and
wherein the first sensor of the plurality of biosensors is covered with a cover when the measurement is not performed.

2. The biosensor arrangement structure according to claim 1,
wherein the auxiliary supporter includes an arm rest for supporting an arm of the occupant, and
wherein a front upper end of the arm rest is a part where the first sensor of the plurality of biosensors is installed, and
wherein the part where the first sensor of the plurality of biosensors is installed includes a housing in the part, and the first sensor of the plurality of biosensors is housed in the housing when the measurement is not performed.

3. The biosensor arrangement structure according to claim 1,
wherein the auxiliary supporter includes a head rest for supporting a head of the occupant, and
wherein a front part of the head rest is a part where the first sensor of the plurality of biosensors is installed.

4. The biosensor arrangement structure according to claim 1,
wherein the auxiliary supporter includes a neck rest for supporting a neck of the occupant, and
wherein a front part of the neck rest is a part where the first sensor of the plurality of biosensors is installed.

5. The biosensor arrangement structure according to claim 1,
wherein the auxiliary supporter includes an ottoman for supporting legs of the occupant, and
wherein a right and/or left part of the ottoman is a part where the first sensor of the plurality of biosensors is installed, and
the ottoman is retracted and is not used while the occupant is driving a vehicle.

6. The biosensor arrangement structure according to claim 5,
wherein the auxiliary supporter includes a foot rest for supporting feet of the occupant,
wherein a right and/or left part of the foot rest is a part where the at least one of the plurality of biosensors is installed, and
wherein the foot rest and the ottoman are connected together to form a L shape to support the legs and the feet of the occupant.

7. The biosensor arrangement structure according to claim 1,
wherein the seat is installed in a vehicle with a driving controller for switching between autonomous driving and manual driving, and the seat is transformable into different forms between in the autonomous driving and in the manual driving, and
wherein the plurality of biosensors measure the health condition in the manual driving, and in response to deterioration of the health condition being detected, the driving controller switches a driving mode to the autonomous driving.

8. The biosensor arrangement structure according to claim 1, wherein the second sensor of the plurality of biosensors is arranged at the seat body in a position that does not interfere with an air pathway for air conditioning.

9. A biosensor arrangement structure, comprising:
a plurality of biosensors that is disposed in a seat for supporting an occupant and that measures a health condition of the occupant,
wherein the seat includes: a seat body for holding the occupant; and an auxiliary supporter for supporting a body part of the occupant except for a torso and thighs,
wherein at least a first sensor of the plurality of biosensors is disposed at the auxiliary supporter,
wherein at least a second sensor of the plurality of biosensors is disposed at the seat body,
wherein the plurality of biosensors includes a photoelectric pulse wave sensor that uses light to measure a pulse wave of the occupant,
wherein the photoelectric pulse wave sensor is disposed under a covering material, and measures the pulse wave through a hole in the covering material,
wherein the photoelectric pulse wave sensor includes a light emitting part and a light receiving part, and
wherein only the light emitting part and the light receiving part are exposed on the covering material forming a surface of the seat body or the auxiliary supporter, and a part other than the light emitting part and the light receiving part of the photoelectric pulse wave sensor is covered with the covering material.

10. The biosensor arrangement structure according to claim 9,
wherein the auxiliary supporter includes an arm rest for supporting an arm of the occupant, and
wherein a front upper end of the arm rest is a part where the first sensor of the plurality of biosensors is installed, and
wherein the part where the first sensor of the plurality of biosensors is installed includes a housing in the part, and the first sensor of the plurality of biosensors is housed in the housing when the measurement is not performed.

11. The biosensor arrangement structure according to claim 9,
wherein the auxiliary supporter includes a head rest for supporting a head of the occupant, and
wherein a front part of the head rest is a part where the first sensor of the plurality of biosensors is installed.

12. The biosensor arrangement structure according to claim 9,
wherein the pulse wave sensor is a piezoelectric pulse wave sensor that measures a pressure wave on a body surface of the occupant to measure the pulse wave of the occupant.

13. The biosensor arrangement structure according to claim 9,
wherein the pulse wave sensor is an electromagnetic pulse wave sensor that uses an electromagnetic wave to measure a pulse wave of the occupant.

14. The biosensor arrangement structure according to claim 9, wherein the seat is installed in a vehicle with a driving controller for switching between autonomous driving and manual driving, and the seat is transformable into different forms between in the autonomous driving and in the manual driving, and
wherein the plurality of biosensors measure the health condition in the manual driving, and in response to deterioration of the health condition being detected, the driving controller switches a driving mode to the autonomous driving.

15. The biosensor arrangement structure according to claim 9,
wherein the second sensor of the plurality of biosensors is arranged at the seat body in a position that does not interfere with an air pathway for air conditioning.

16. A biosensor arrangement structure, comprising:
a plurality of biosensors that is disposed in a seat for supporting an occupant and that measures a health condition of the occupant,
wherein the seat includes: a seat body for holding the occupant; and an auxiliary supporter for supporting a body part of the occupant except for a torso and thighs,
wherein at least a first sensor of the plurality of biosensors is disposed at the auxiliary supporter,
wherein at least a second sensor of the plurality of biosensors is disposed at the seat body,
wherein the auxiliary supporter is movable or retractable, and
wherein in response to a movement or retraction of the auxiliary supporter, the first sensor of the plurality of biosensors starts or stops the measurement.

17. The biosensor arrangement structure according to claim 16,
wherein the auxiliary supporter includes an arm rest for supporting an arm of the occupant, and
wherein a front upper end of the arm rest is a part where the first sensor of the plurality of biosensors is installed, and
wherein the part where the first sensor of the plurality of biosensors is installed includes a housing in the part, and the first sensor of the plurality of biosensors is housed in the housing when the measurement is not performed.

18. The biosensor arrangement structure according to claim 16,
wherein the auxiliary supporter includes an ottoman for supporting legs of the occupant, and
wherein a right and/or left part of the ottoman is a part where the first sensor of the plurality of biosensors is installed, and
the ottoman is retracted and is not used while the occupant is driving a vehicle.

19. The biosensor arrangement structure according to claim 16,
wherein the seat is installed in a vehicle with a driving controller for switching between autonomous driving and manual driving, and the seat is transformable into different forms between in the autonomous driving and in the manual driving, and
wherein the plurality of biosensors measure the health condition in the manual driving, and in response to deterioration of the health condition being detected, the driving controller switches a driving mode to the autonomous driving.

20. The biosensor arrangement structure according to claim 16,
wherein the second sensor of the plurality of biosensors is arranged at the seat body in a position that does not interfere with an air pathway for air conditioning.

* * * * *